United States Patent
Berger et al.

(10) Patent No.: US 6,685,828 B2
(45) Date of Patent: Feb. 3, 2004

(54) AUTOMATED SAMPLE COLLECTION IN SUPERCRITICAL FLUID CHROMATOGRAPHY

(75) Inventors: Terry A. Berger, Newark, DE (US); Kimber D. Fogelman, Hockessin, DE (US); Kenneth Klein, Newark, DE (US); L. Thompson Staats, III, Lincoln University, PA (US); Mark Nickerson, Landenburg, PA (US); Paul F. Bente, III, Landenburg, PA (US)

(73) Assignee: Berger Instruments, Inc., Newark, DE (US)

( * ) Notice: Subject to any disclaimer, the term of this patent is extended or adjusted under 35 U.S.C. 154(b) by 37 days.

(21) Appl. No.: 10/119,529

(22) Filed: Apr. 9, 2002

(65) Prior Publication Data

US 2002/0144949 A1 Oct. 10, 2002

Related U.S. Application Data

(63) Continuation-in-part of application No. 09/607,316, filed on Jun. 26, 2000, now Pat. No. 6,413,428.
(60) Provisional application No. 60/154,038, filed on Sep. 16, 1999.

(51) Int. Cl.[7] .............................................. B01D 15/08
(52) U.S. Cl. .................... 210/198.2; 210/656; 210/659
(58) Field of Search ................. 210/634, 635, 210/656, 659, 137, 198.2, 511, 541; 95/82, 87; 96/101, 102; 422/70

(56) References Cited

U.S. PATENT DOCUMENTS

| | | | | |
|---|---|---|---|---|
| 3,374,607 A | * | 3/1968 | Fisher | 55/67 |
| 4,168,955 A | * | 9/1979 | Allington | 23/230 R |
| 4,478,720 A | | 10/1984 | Perrut | 210/659 |
| 4,845,985 A | | 7/1989 | Berger | 73/23 |
| 4,962,662 A | | 10/1990 | Berger | 73/23.42 |
| 5,139,681 A | | 8/1992 | Cortes | 210/659 |
| 5,198,115 A | | 3/1993 | Stalling | 210/634 |
| 5,234,599 A | | 8/1993 | Cortes | 210/659 |
| 5,322,627 A | | 6/1994 | Berger | 210/656 |
| 5,340,476 A | | 8/1994 | Berger | 210/198.2 |
| 5,584,989 A | | 12/1996 | Jameson | 21/137 |
| 5,601,707 A | | 2/1997 | Clay | 210/198.2 |
| 5,620,663 A | * | 4/1997 | Aysta | 422/104 |
| 5,843,311 A | | 12/1998 | Richter | 210/634 |
| 5,996,818 A | | 12/1999 | Boje | 211/74 |
| 6,413,428 B1 | * | 7/2002 | Berger | 210/634 |
| 6,428,702 B1 | * | 8/2002 | Berger | 210/656 |
| 6,558,540 B2 | * | 5/2003 | Berger | 210/198.2 |
| 6,576,125 B2 | * | 6/2003 | Berger | 210/198.2 |

FOREIGN PATENT DOCUMENTS

| | | | |
|---|---|---|---|
| DE | 2843920 | * | 4/1980 |
| WO | WO9857181 | * | 12/1998 |

OTHER PUBLICATIONS

Berger, Terry A: *Separation of polar solutes by packed column supercritical fluid chromatography*, Journal of Chromatography, A 785 (1997) 3–33.
Berger, T.A.: Packed Column SFC, The Royal Society of Chemistry 1995, pp. 3–150.

* cited by examiner

Primary Examiner—Ernest G. Therkorn
(74) Attorney, Agent, or Firm—Zito tlp; Joseph J. Zito; Kendal M. Sheets

(57) ABSTRACT

A system for collection of liquid phase sample fractions from a supercritical fluid chromatography system is disclosed. The system has different ways of gathering the liquid phase into a collection chamber and provides for automated removal of liquid phase from a collection chamber into separate collection container. A separate pressure scheme is invoked upon the collection chambers to move liquid phase out of a chamber and into the separate collection container. In addition, the invention provides a renewal system for the collection chambers where each chamber returns to an uncontaminated stated by washing with a cleaning solution after removal of collected liquid phase. Spent cleaner from a chamber is purged using the pressure system into a waste stream for disposal.

14 Claims, 14 Drawing Sheets

AUTOMATED SAMPLE COLLECTION IN SUPERCRITICAL FLUID CHROMATOGRAPHY

CROSS REFERENCE TO RELATED APPLICATIONS

This application is a continuation in part of application Ser. No. 09/607,316 APPARATUS AND METHOD FOR PREPARATIVE SUPERCRITICAL FLUID CHROMATOGRAPHY, filed Jun. 26, 2000, now U.S. Pat. No. 6,413,428, which claims the priority of provisional application No. 60/154,038, filed Sept. 16, 1999.

BACKGROUND OF THE INVENTION

A substantial need exists for industries to recover purified components of interest from samples containing simple or complex mixtures of components. Many technologies have been developed to meet this need. For dissolvable, nonvolatile components, the technology of choice has been liquid elution chromatography.

Analysts have several objectives in employing preparative elution chromatography. First, they wish to achieve the highest available purity of each component of interest. Second, they wish to recover the maximum amount of the components of interest. Third, they wish to process sequential, possibly unrelated samples as quickly as possible and without contamination from prior samples. Finally, it is frequently desirable to recover samples in a form that is rapidly convertible either to the pure, solvent-free component or to a solution of known composition which may or may not include the original collection solvent.

In the case of normal phase chromatography, where only organic solvents or mixtures are used as eluants, typical fraction volumes of tens to hundreds of millimeters are common. The fraction must then be evaporated over substantial time to recover the component residues of interest. In reversed phase chromatography, where mixtures of organic solvents and water are used as the elution mobile phase, a secondary problem arises. After removal of lower boiling solvents, recovered fractions must undergo a water removal step lasting from overnight to several days. Thus, availability of the recovered components of interest is delayed by hours or days, even after the separation process is complete. This latter problem can create a serious bottleneck in the entire purification process when enough samples are queued.

Where difficult separation conditions exist or separation speed is a requirement, a subset of elution chromatography, known as high performance liquid chromatography (HPLC), is preferred. This HPLC technique is used both as an analytical means to identify individual components and as a preparative means of purifying and collecting these components.

For analytical HPLC, samples with component levels in the nanogram to microgram range are typical. Preparative HPLC systems typically deal with microgram to multiple gram quantities of components per separation. Preparative HPLC systems also require a means to collect and store individual fractions. This is commonly performed, either manually or automatically, simply by diverting the system flow stream to a series of open containers.

Drawbacks exist to the current use of preparative HPLC. Elution periods ranging from several minutes to hours are necessary for each sample. Further, even in optimal conditions only a small fraction of the mobile phase contains components of interest. This can lead to very large volumes of waste mobile phase being generated in normal operation of the system.

An alternative separation technology called supercritical fluid chromatography (SFC) has advanced over the past decade. SFC uses highly compressible mobile phases, which typically employ carbon dioxide ($CO_2$) as a principle component. In addition to $CO_2$, the mobile phase frequently contains an organic solvent modifier, which adjusts the polarity of the mobile phase for optimum chromatographic performance. Since different components of a sample may require different levels of organic modifier to elute rapidly, a common technique is to continuously vary the mobile phase composition by linearly increasing the organic modifier content. This technique is called gradient elution.

SFC has been proven to have superior speed and resolving power compared to traditional HPLC for analytical applications. This results from the dramatically improved diffusion rates of solutes in SFC mobile phases compared to HPLC mobile phases. Separations have been accomplished as much as an order of magnitude faster using SFC instruments compared to HPLC instruments using the same chromatographic column. A key factor to optimizing SFC separations is the ability to independently control flow, density and composition of the mobile phase over the course of the separation.

SFC instruments used with gradient elution also reequilibrate much more rapidly than corresponding HPLC systems. As a result, they are ready for processing the next sample after a shorter period of time. A common gradient range for gradient SFC methods might occur in the range of 2% to 60% composition of the organic modifier.

It is worth noting that SFC instruments, while designed to operate in regions of temperature and pressure above the critical point of $CO_2$, are typically not restricted from operation well below the critical point. In this lower region, especially when organic modifiers are used, chromatographic behavior remains superior to traditional HPLC and often cannot be distinguished from true supercritical operation.

In analytical SFC, once the separation has been performed and detected, the highly compressed mobile phase is directed through a decompression step to a flow stream. During decompression, the $CO_2$ component of the mobile phase is allowed to expand dramatically and revert to the gas phase. The expansion and subsequent phase change of the $CO_2$ tends to have a dramatic cooling effect on the waste stream components. If care is not taken, solid $CO_2$, known as dry ice, may result and clog the waste stream. To prevent this occurrence, heat is typically added to the flow stream. At the low flow rates of typically analytical systems only a minor amount of heat is required.

While the $CO_2$ component of the SFC mobile phase converts readily to a gaseous state, moderately heated liquid organic modifiers typically remain in a liquid phase. In general, dissolved samples carried through SFC system also remain dissolved in the liquid organic modifier phase.

The principle that simple decompression of the mobile phase in SFC separates the stream into two fractions has great importance with regard to use the technique in a preparative manner. Removal of the gaseous $CO_2$ phase, which constitutes 50% to 95% of the mobile phase during normal operation, greatly reduces the liquid collection volume for each component and thereby reduces the post-chromatograhic processing necessary for recovery of separated components.

A second analytical purification technique similar to SFC is supercritical fluid extraction (SFE). Generally, in this technique, the goal is to separate one or more components of interest from a solid matrix. SFE is a bulk separation technique, which does not necessarily attempt to separate individually the components, extracted from the solid matrix. Typically, a secondary chromatographic step is required to determine individual components. Nevertheless, SFE shares the common goal with prep of SFC of collecting and recovering dissolved components of interest from supercritical flow stream. As a result, a collection device suitable for preparative SFC should also be suitable for SFE techniques.

Expanding the technique of analytical SFC to allow preparative SFC requires several adaptations to the instrument. First the system requires increased flow capacity. Flows ranging from 20 ml/min to 200 ml/min are suitable for separation of multi-milligram up to gram quantities of materials. Also, a larger separation column is required. Finally, a collection system must be developed that will allow, at a minimum, collection of a single fraction of the flow stream which contains a substantially purified component of interest. In addition, there frequently exists a compelling economic incentive to allow multiple fraction collections from a single extracted sample. The modified system must also be able to be rapidly reinitialized either manually or automatically to allow subsequent sample injection followed by fraction collection.

Several commercial instances of preparative SPC instrumentation have been attempted which have employed different levels of technology to solve the problems of collection. A representative sampling of these products includes offerings from Gilson, Thar, Novasep, and ProChrome. However, no current implementation succeeds in providing high recovery, high purity, and low carryover from sample to sample. For example, one system may use the unsophisticated method of simply spraying the collection stream directly into a large bottle, which results in high sample loss, presumably due to aerosol formation. Another system uses a cyclonic separator to separate the two streams, but provides no rapid or automated means of washing the separators to prevent carryover. Such instruments are typically employed to separate large quantities of material by repetitive injection so that no sample-to-sample cleaning step is required. Other systems use a collection solvent to trap a sample fraction into a volume of special solvent in a collection container. This technique uses relatively large quantities of hazardous solvents to perform sample collection, is prone to sample fraction concentration losses or degradation, and possible matrix interferences exist between fractionated samples and collection solvent constituents.

An example of a SFC system is illustrated outside of the outlined section 10 in FIG. 1. The schematic flow diagram is a packed-column supercritical fluid chromatography (SFC) system from initial modifier supply to a detector. The system has a carbon dioxide supply tank 200, line chiller 220, pump 202, modifier tank 204 and pump 206, dampener and pressure transducer 208, leading to a mixing column 210, connected to an injection valve 212 that is connected to at least one packed chromatography column 214, and a detector 216.

In a SFC system, liquefied compressed carbon dioxide gas is supplied from cylinders 200. High pressure tubing 218 connects the carbon dioxide reservoir tank 200 to the carbon dioxide pump 202. The tubing may be cooled 220 prior to connecting to the pump 202. The system uses two HPLC-type reciprocating pumps 202, 206. One pump 202 delivers carbon dioxide and the other pump 206 delivers modifier 204, such as methanol. The carbon dioxide and modifier are combined, creating a mixture of modifier dissolved into the supercritical fluid.

The combined supercritical fluid is pumped at a controlled mass-flow rate from the mixing column 210 through transfer tubing at a fixed-loop injector 212 where the sample of interest is injected into the flow system. The sample combines with the compressed modifier fluid inside the injection valve 212 and discharges into at least one packed chromatography column 214. After fractionation of the sample occurs in the columns 214, the elution mixture passes from the column outlet into a detector 216.

SFC is finding significant advantages in the separation of enantiomers and is supplanting normal-phase HPLC for performing chiral separations. The majority of chiral separation by SFC have been performed using packed columns with binary or ternary mobile phases. SFC can also be used as an alternative to the reversed-phase HPLC or polar organic modes used with columns in HPLC. Extremely rapid separations, up to less than a minute, with relatively high resolution are possible. Using binary mobile phases, SFC has been used to derivatize highly polar compounds in order to elute less polar entities with binary mobile phase. Tertiary mobile phases are often used in chiral separations since most are performed in the pharmaceutical industry, and a large fraction of drugs, drug intermediates and metabolites are aliphatic or polyfunctional amines.

SUMMARY OF THE INVENTION

The present invention relates to sample recovery after separation by supercritical fluid chromatography or supercritical fluid extraction, and improvements therein. More specifically, the present invention provides a method and device to collects fractionated components of sample solutes into one or more collection containers in a more efficient and faster manner while generating less spent solvents for disposal.

More specifically, the present invention relates to optimally separating a liquid phase, containing sample components of interest, from a much larger gaseous phase after the controlled expansion, or decompression, of a single chromatographic mobile phase from a high working pressure to a lower pressure where it is unstable. The controlled decompression causes a phase separation between liquid and gaseous phases while at the same time aerosol formation is strongly suppressed within the transfer tubing.

It is a further object of the present invention to provide a device and method to separate monophasic fluids that are mixtures of highly compressed or liquefied gasses and organic liquid modifiers into gaseous and liquid phases inside transfer tubing prior to collection of fractions of the liquid phase into one or more unique collection chambers. The collection of fractions of the liquid phase into collection chambers minimizes liquid solvent use and waste through efficient gas and liquid phase separation prior to entering collection chambers. The collection technique uses no additional solvents for collection of fractions.

This invention provides a cassette bank of multiple chambers to collect and store separated or extracted fractions. Each collection cassette includes one or more collection chambers, and each chamber can receive a purified liquid fraction. Each chamber may hold a removable sample collection liner. The collection liners may be individually removed, substituted, stored, cleaned and re-used, or discarded. One purpose of the collection liner is to provide a simplified means of transporting the collected liquid fraction from the cassette. A second purpose of the collection liner is to provide a means to eliminate cross-contamination of consecutive samples by providing an easily replaceable, uncontaminated liner in each collection chamber for each sample.

The present invention manually or automatically controls one or more valves and a sealing mechanism for collection chambers such that multiple liquid phase fractions from one sample may be collected into one or more chambers without mechanically adjusting the collection chamber seals. This method allows for rapid switching between collection chambers in the event of closely separated peaks in the chromatographic flow stream.

It is a further object of the present invention to facilitate a manual or automatic reset of the collection system to allow consecutive samples to be processed in a rapid manner. Technical difficulties arise in the implementation of a collection system that satisfies all the analysts objectives stated above. The major problem centers around the tremendous expansion (typically 500-fold) of the pressurized liquid or supercritical $CO_2$ fraction of the mobile phase that violently transforms into a gas at atmospheric pressure. This transition has four major negative effects with regard to liquid phase sample collection.

First, as mentioned above, the expanding $CO_2$ causes a severe temperature drop that has the possibility of forming dry ice and clogging the system. Since flows of preparative SFC systems are much higher than corresponding analytical systems, considerable more heat must be added to compensate for the temperature drop. Care must be taken; however, not to allow the actual temperature to rise in the flow system since this may cause damage to thermally unstable compounds of interest. Higher organic modifier content reduces the severity of this problem, both by adding heat capacity and by dissolving the $CO_2$, thereby preventing dry ice formation.

Second, as the $CO_2$ expands, it rapidly loses any solvating power it had in the compressed state. If components of interest are largely dependent on the $CO_2$ for solubility they will lose their primary means of transport through the flow system. Solid components will accumulate and eventually clog the flow path causing system failure. Again, the organic modifier component is an important factor here since the liquid will continue to solvate the components of interest and transport them to a collection device. Care must be taken not to introduce too much heat into the flow stream as to drive the organic modified also into the gas phase, otherwise its beneficial effect of transporting the solutes will be lost.

Third, it is beneficial to complete the transition from liquid to gaseous $CO_2$ in as short a period as possible after the initial decompression stage. While in the liquid state, $CO_2$ can disperse the organic modifier containing components of interest even when it is not dense enough to have any significant solvating power. The dispersion can have the effect of remixing components that had been efficiently separated by the SFC process prior to decompression. The faster the $CO_2$ can be converted the less chromatographic degradation can occur. Two factors seem to predominate in controlling the ability to volatilize the liquid phase $CO_2$: (a) efficient heat transfer between the heat source and the flowing liquid, and (b) residence time of the $CO_2$ in the heated region. The first factor can be positively affected by selection of a highly conductive material such as copper for heater fabrication. Insuring excellent thermal contact between the heater and a thin-walled transfer tubing also facilitates heat transfer to the flowing fluids. Residence time of the decompressing fluid can be controlled by stepping the pressure drop over a series of one or more restrictors in the transfer line. Higher backpressure slows the linear velocity of the biphasic fluid in the heater. So long as the back pressure generated by these restrictions do not interfere with the SFC density regulation in the high pressure separation region, a great deal of turnability is possible for optimizing heat transfer.

Fourth, due to the expansion, linear velocities of the depressurizing fluid increase dramatically in the transfer tubing. Residual liquids of the system are moved along the flow path largely by shear forces from the expanding gas. This turbulent environment is ideal for the creation of aerosols, whereby very small droplets of modifier liquid are entrained in the gas phase as a "mist." It is a finding of this study that the aerosol formation within the transfer tubing can be almost completely controlled by proper temperature control of the expanding two-phase system. Aerosol formation is a greater problem at lower temperatures. It is a surprising finding of this work that higher levels of organic modifier with correspondingly lower $CO_2$ content require higher temperature levels to prevent visible aerosol formation.

In the preferred exemplary embodiment, the SFC collection system is composed of a moderately restrictive, thermally regulated stainless steel transfer tube which extends from a back pressure regulation component of the SFC chromatograph into a multi-port distribution valve and from the valve to a variety of flow paths leading either through discrete collection chambers or directly connected to a vented common waste container.

Initial separation of the liquid phase sample from carbon dioxide gas occurs immediately at the point of initial decompression within the backpressure regulator of the SFC or SFE instrument. By providing downstream restriction, a minimum backpressure sufficient to prevent the formation of solid $CO_2$ can be maintained while liquid $CO_2$ is present in the transfer lines.

The remainder of the $CO_2$ evaporation and separation from the organic modifier occurs in the stainless steel transfer tubing prior to entering the cassette. This is accomplished by exposing the transfer tubing to a series of one or more heaters designed to optimize thermal transfer to the fluid. Ideally, this heater series transfers sufficient energy to the liquid $CO_2$ portion of the emerging fluid to allow for complete evaporation of the liquid $CO_2$ and raise the fluid temperature sufficiently to prevent the transfer tubing from icing externally. Because rates of heat transfer are time dependent, it is beneficial to slow the velocity of fluids within the heater series.

During the $CO_2$ evaporation process within the first heated zone, significant separation between the gaseous $CO_2$ and liquid modifier occurs. However, the separation to pure $CO_2$ and pure organic modifier is never realized for several reasons. First, some organic modifier is typically also evaporated into the gas state. The degree of evaporation is largely dependent on the absolute temperature of the fluids within the transfer tubing. While organic modifier evaporation does lead to lower recovery of liquid phase, it does not necessarily reduce the recovery of dissolved components of interest which do not typically have low enough boiling points to convert to vapor. Second, a fraction of $CO_2$ will remain dissolved in the organic liquid. Both temperature and pressure determine the amount of residual $CO_2$. Higher temperatures reduce CO2 solubility while higher pressures increase CO2 solubility.

Aerosol formation of the liquid phase is a common problem in SFC sample collection and is a primary cause of loss of the organic liquid phase that contains the dissolved components of interest. Higher temperatures reduce the aerosol generation. The composition of the separated phases also is a factor. Higher temperatures are required to eliminate aerosols in streams with higher organic liquid composition. An additional heated zone is used to trim the fluid temperature to control aerosols. In addition, this heater provides a fine level of temperature control of the fluid before collection in the pressurized collection chamber. As mentioned above, a secondary effect is that a higher trim temperature can reduce the concentration of dissolved CO2, thereby reducing the possibility of uncontrolled or explosive outgassing of the CO2 when the pressure is removed from the collection chamber.

Following the trim heater, a valve system is used to divert the biphasic flow stream sequentially to waste or to one of the collection chambers in a collection cassette. The valve system is comprised of one or more valves and an electronic controller. The system is designed to offer rapid response to a manual or automated start/stop signal. Typically, the signal would result from detection of a component of interest emerging from the high-pressure flow system. A start signal would be generated at the initial detection of the component while a stop signal would be generated at the loss of detection. The effect of a start signal is to divert the flow to the first unused collection chamber of the cassette. The effect of the stop signal is to divert the flow to waste. Another possible type of start/stop signal may be based on a timetable rather than physical detection of components. The controller may also have features to limit the access time or flow volume allowed to an individual chamber. In addition, the controller may allow or prevent the system from cycling back to the original chamber if more fractions are desired than there exists available collection chambers.

The collection cassette is a resealable apparatus that contains one or more hollow collection chambers open at the top. In the preferred exemplary embodiment, each chamber holds a removable inert liner. The liner collects a fraction of the original sample dissolved in a liquid solvent base. A preferred exemplary embodiment of a cassette has four chambers housing four test tube vials that function as chamber liners. The number of chambers in a cassette may be varied with no effect on performance. Each test tube vial may hold up to its capacity of a separated sample fraction from the high-pressure flow stream.

In the preferred embodiment, sample fractions are collected in one chamber of the cassette at a time. The biphasic fluid enters a chamber via a transfer line from the valve system. The tip of the transfer line is preferentially positioned tangential to the inner wall of the collection tube and with a slight downward angle, usually less than 45 degrees from horizontal. Attached to the transfer line and suspended inside a test tube is a guiding spring wire. The spring wire is bowed away from the transfer line and functions as a guide for the transfer line as it descends into a vial. When transfer tubing is properly inserted into a test tube vial, the bowed section of the spring wire engages the circumferential edge of the open end of a test tube vial. As the tubing continues into the test tube, the spring wire compresses against the inner surface of the test tube vial and pushes the tubing toward the opposite side of the vial. As a result, the angled tip of the transfer tubing is pressed against the inner wall of the test tube vial.

Both the organic liquid and CO2 gas follow a descending spiral path along the inner wall to the bottom of the collection liner. The CO2 gas continues in a path up the center of the liner to a vent in the collection chamber. A restrictive transfer line attached to the vent causes the CO2 gas to pressurize the collection chamber both inside and outside the collection liner. The degree of black pressurization within the chamber is roughly proportional to the composition of CO2 in the original mobile phase.

The pressurization of the collection chamber serves to slow down the velocity of the CO2 entering the chamber. This in turn reduces the magnitude of shear forces occurring between the CO2 gas and the collected liquid at the bottom of the liner. With lower shear forces, there is less tendency for the collected liquid to become an aerosol and to be removed from the collection tube with the existing gas. A similar effect is obtained by the proper angling the inlet transfer line relative to the collection tube wall. The closer the angle of the tube is to horizontal the lower the observed turbulence at the liquid surface. However, enough angle must be provided to ensure the majority of effluent is directed downward rather than upward on the liner wall. The two effects of back pressure and delivery angle combine to reduce aerosol formation in the collected liquid fraction. The success of optimizing these effects determines how close the inlet tube can come to the collection liquid, and thereby determining how high the liner may be filled before sample loss becomes a problem. When flow to the chamber is stopped, the chamber depressurizes. Once the sample chamber is depressurized, the liner may be removed by opening the top lid of the cassette.

The collection of fractions into disposable liners of collection chambers may be automated through the use of robotics. An automated system enables rapid substitution of test tube vials into and out of collection chambers and long unattended run times based on a quantity of vials available for substitution. A programmable robot automatically sequences cassettes between sample injections, thereby speeding up the process while reducing the margin for error. The automated system can collect on the order of thousands of fractions per month.

The automated system is contained in laboratory grade housing. The system is comprised of a robotic arm, a supply of test tube vials arranged upright in racks, and an automated version of a cassette assembly. In addition, the system may contain sufficient probes, valves and sample containers to achieve automated delivery of unfractioned samples into the chromatographic or extraction system.

The collection cassette and its automated mechanisms are designed for rapid sample collection and minimal stop time between chamber liner replacements. The cassette in the preferred embodiment has two banks of four collection chambers each. A lid is positioned above one bank of collection chambers in the cassette. The lid has four partially recessed annular bores corresponding to the four collection chambers in the cassette. The lid raises and lowers with action from pneumatic actuators mounted on the base of the housing and located an opposite longitudinal end of the lid. As the actuators simultaneously lower the lid onto the collection cassette, the top edge of each chamber engages the bottom edges of the lid corresponding to the rims of each partially recessed bore. The lid and chambers engage and form pressure tight seals in each chamber in preparation for sample fraction collection. The lid has transfer and waste line tubing passing through each recessed bore that correspond to each collection chamber. Each tubing pair enters a test tube as the lid is lowered onto the cassette. The spring wire attached to the inlet tubing guides an inlet tube into a test tube vial. An angled tip on the tube is forced against the inner wall of the test tube. As the lid has sealed on the row of collection chambers, a valve system dispenses the flow stream containing gaseous and liquid phases into the chamber liners from the sample fractionation process.

When all test tube vials in the pressurized cassette row have been filled and depressurized, the lids lifts off of the cassette. The cassette then moves laterally, or shuttles, until a row containing empty collection chamber liners is moved under the lid in place of the former row. The cassette is constrained to shuttle laterally along a path on the base of the housing. The lid lowers and engages the new row of chambers, thereby preparing the test tubes to accept sample fractions. Meanwhile, the former new row of chamber liner test tube vials containing liquid fractions are removed from the collection chambers and transported to open spaces in a storage tray via a robot arm.

In summary, samples in the preferred embodiment are dissolved in a minimum volume of modifier solvent and are collected in removable and reusable liners. Through controlling flowrate, velocity, temperature and pressure in the system, superior separation of near-supercritical elution fluid is obtained. Collection efficiencies of up to 98% of injected sample components may be realized. The cassette, by utilizing pressurized collection and cleaning solvent spent by the laboratory, which is economical and good for the environment. Laboratories and research facilities that demand purity of samples while maximizing output and minimizing waste will benefit from the proposed invention. Large-scale sample fractionation and collection, numbering in the thousands of samples per month, may be realized from the exemplary embodiment.

The method and its associated apparatus, described herein, provides for rapid separation and collection of volumes of the sample fractions from supercritical fluid chromatography systems such as those used in chiral separations. An exemplary embodiment is described using repetitive injections of higher volumes of samples into the system to effect rapid processing and recovery rates from similar elution components through a chromatography column. In contrast, analytical chromatography methods pertain to recovering multiple sample fractions that are separated and each gathered into different collection devices. The processing and separation method and apparatus for this exemplary embodiment is described in the specification.

Referring to the schematic diagram in FIG. 11, an alternative exemplary embodiment of the present invention is illustrated. Generally, the alternative embodiment provides a system for collection of liquid phase sample fractions that is similar to the preferred embodiment but has ways of gathering the liquid phase into a final collection point and renewing collection chambers. The systems of the present invention can also be automated for efficient, high-speed sample collection. The alternative embodiment permits removal of liquid phase from a collection chamber without using a removable liner. A separate pressure scheme is invoked upon the collection chambers to move liquid phase out of a chamber and into a separate collection container.

In addition, the alternative embodiment provides a renewal system for the collection chambers where each chamber returns to an uncontaminated state through washing with a cleaning solution after removal of collected liquid phase into a final collection point. Spent cleaner from a chamber is purged using the pressure system into a waste stream for disposal. The alternative embodiment is additionally applied to the shuttle cassette system, described according to the embodiment shown in FIG. 4. Using an automated shuttle comprising two cassette banks of four chambers each, a first bank of chambers can receive liquid phase fractions from the SFC system, while liquid phase can be simultaneously removed from a second cassette bank. The chambers of the second bank are then renewed by the cleaning system and prepared for reception again of liquid phase sample fractions.

BRIEF DESCRIPTION OF THE DRAWINGS

For a better understanding of the nature of the present invention, reference is had to the following figures and detailed description, wherein like elements are accorded like reference numerals, and wherein.

DETAILED DESCRIPTION OF PREFERRED EXEMPLARY EMBODIMENTS

Figure 1:
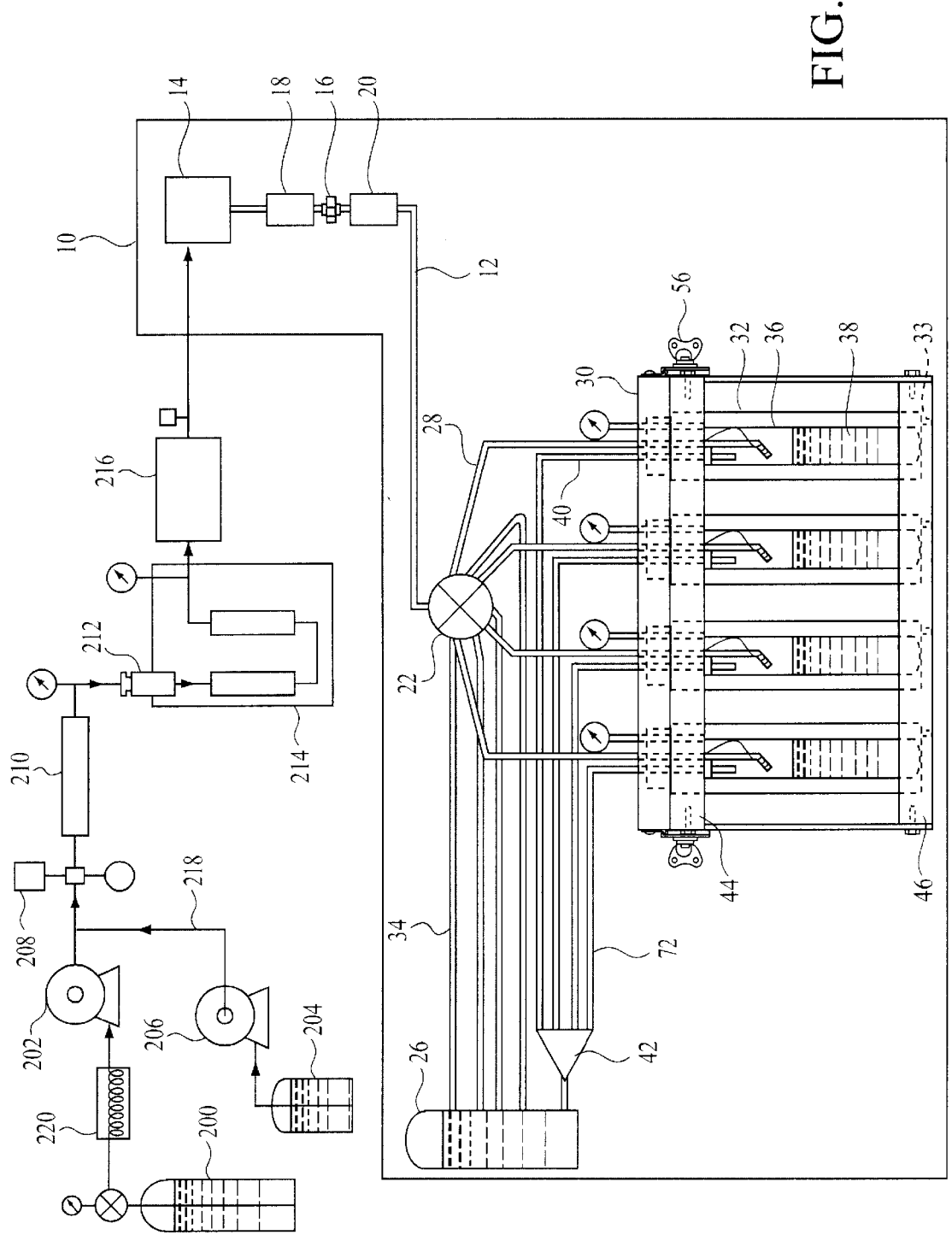
FIG. 1 illustrates a schematic flow diagram of the supercritical fluid chromatography system and the collection system including the sample cassette embodied in the invention.

The preferred embodiment of the apparatus is illustrated in the flow chart of FIG. 1 within the perimeter line 10. Except where noted, specifications for a preferred exemplary embodiment are given for a system that accepts flows of 20 to 100 ml/min total flow ($CO_2$ plus modifier flow) in the highly compressed state from the pumping system. Flowrates for alternative embodiments could range in orders of magnitude higher or lower through adjustment or substitution of system hardware and flow parameters.

In the preferred exemplary embodiment, the SFC collection system is composed of a moderately restrictive, thermally regulated transfer tube 12 which extends from a back pressure regulator 14 into a multi-port distribution valve 22 and from the valve to a variety of flow paths leading either through discrete collection chambers 32 or directly connected to a vented common waste container 26.

Expanded elution fluid leaves the backpressure regulator 14 at a velocity of approximately two to five times the flow velocity upstream of the backpressure regulator 14 and under backpressure of approximately twenty to forty bars. Variations in the expansion occur as a result of the changing modifier solvent concentration from 2.5 to 50 percent over the course of a separation.

Initial separation of the liquid phased sample from carbon dioxide gas occurs immediately at the point of initial decompression within the backpressure regulator 14 of the SFC or SFE system. By providing downstream restriction, a minimum backpressure sufficient to prevent the formation of solid $CO_2$ can be maintained while liquid $CO_2$ is present in the transfer lines 12. The degree of $CO_2$ evaporation is a function of both the available heat transfer in this region and the downstream flow restriction which limits the amount of expansion available to the decompressing fluid. Due to the pressure drop across the backpressure regulator 14, a fraction of the emerging $CO_2$ will evaporate, typically causing a significant drop in the temperature of the emerging fluid.

Further separation and evaporation of $CO_2$ from the organic modifier occurs in stainless steel transfer tubing 12 running between the first backpressure regulator 14 and the cassette 24. The transfer tubing 12 containing a flow stream of the biphasic $CO_2$ and modifier is exposed to a series of heaters 16, 18 designed to optimize thermal transfer to the biphasic fluid in the flow stream. Ideally, this heater series transfers sufficient energy to the liquid $CO_2$ portion of the emerging fluid to allow for complete evaporation of the liquid $CO_2$ and raises the fluid temperature sufficiently to prevent ice from forming externally on the transfer tubing 12.

During the $CO_2$ evaporation process within the first heated zone, significant separation between the gaseous $CO_2$ and liquid modifier occurs. However, the separation to pure $CO_2$ and pure organic modifier is never realized. Some organic modifier is typically evaporated into the gas state. The degree of evaporation is largely dependent on the absolute temperature of the fluids within the transfer tubing 12. While organic modifier evaporation does lead to lower recovery of liquid phase when it reaches the collection cassette 24, it does not necessarily reduce the recovery of dissolved components of interest which do not typically have low enough boiling points to convert to vapor. A fraction of $CO_2$ will also remain dissolved in the organic liquid modifier. Both temperature and pressure determine the amount of residual $CO_2$. Higher temperatures reduce $CO_2$ solubility while higher pressures increase $CO_2$ solubility. Turbulent flow of the $CO_2$ gas within the narrow tubing also produces a strong shearing force that propels the liquid down the walls of the transfer tube 12. This very turbulent flow frequently causes small droplets at the liquid surface to rip away from the bulk liquid and become entrained into the rapidly moving gas phase of the fluid down the transfer tube 12. Such an effort is called aerosol formation, or "misting."

A plurality of heaters may be mounted in series to heat t the elution fluid. In FIG. 1, the preferred exemplary embodiment has an evaporator heater 18 and a trim heater 20 mounted in series after the backpressure regulator 14. The evaporator 18 is heated with an appropriately sized cartridge heater and controlled by an appropriate heater controller. In the preferred embodiment, transfer tubing 12 is tightly coiled around the heating assembly and optimized for thermal contact. The elution fluid is heated to within the control temperature of the evaporator 18, which is between approximately 5 to 50 degrees C., to protect heat sensitive compounds from being damaged. The objective is to boil $CO_2$ out of the elution fluid as the fluid passes through the evaporator 18. To complete the required heat transfer, biphasic elution fluid inside transfer tubing 12 enters the final heat exchanger, which is a trim heater 20. In the preferred embodiment, the trim heater setting is typically above the evaporator 18 setpoint. The heater 20 is used not only to suppress aerosol formation within the transfer tube 12 but also to control the level of dissolved $CO_2$ in the liquid phase.

It is beneficial to slow the velocity of fluids within the transfer tubing 12 passing through the heater series 18, 20. The fluid velocity is slowed inside the transfer tubing by 12 placing a restrictive orifice or smaller diameter tube immediately downstream from first heater series. Elution fluid exits the evaporator 18 and enters a flow restrictor 16, which provides a higher backpressure in the evaporator 18 and thereby slows the flow and increases the contact time of the liquid $CO_2$ phase. The restrictor 16 also insures a high enough backpressure to prevent the liquid carbon dioxide from forming solid carbon dioxide, also known as dry ice. The restriction increases the backpressure in the heated zone and reduces the amount of gas expansion. In an alternative exemplary embodiment, the velocity of fluids can be slowed after all heaters, however, such a configuration does not control the final expansion of $CO_2$ which can result in uncontrolled cooling of fluids within the transfer lines. As a result, the ability to actively suppress aerosol formation may be diminished.

After existing the trim heater 20, transfer tubing 12 connects to the common port of a valve system 22. The valve system in the preferred exemplary embodiment is a multi-port sector valve 22. As elution fluid from the peak of interest passes through the valve system 22, the gas and liquid phases are directed into either a collection cassette 24 or to a waste stream container 26. The outlet ports on a multi-port selection valve 22 are connected to a plurality of transfer tubing lines 28. The transfer lines 28 pass through a cassette lid 30 and into discrete chambers 32 within the cassette 24. The transfer lines 28 have airtight and pressure resistant connections into and out of the cassette lid 30. The remaining ports in a multi-port selection valve 22 connect to waste transfer lines 34. In an alternative exemplary embodiment, multiple discrete valves are installed and connected to the incoming transfer line 12, having each valve port connected to an individual collection chamber 32 in the cassette 24 and a discrete valve connected to a waste line 34.

Inlet lines 28 entering a collection chamber 32 insert into a test tube vial 36 within a chamber 32. Liquid phase 38 is captured in a test tube 36 while gaseous phase escapes out of a chamber 32 through a discharge line 40. Gas in the discharge line 40 is flowing at high pressure. Discharge lines 40 from the cassette 24 run through a pressure relief switch 42 to protect the cassette and upstream components from possible damage due to over-pressurization from a system malfunction.

Figure 2:
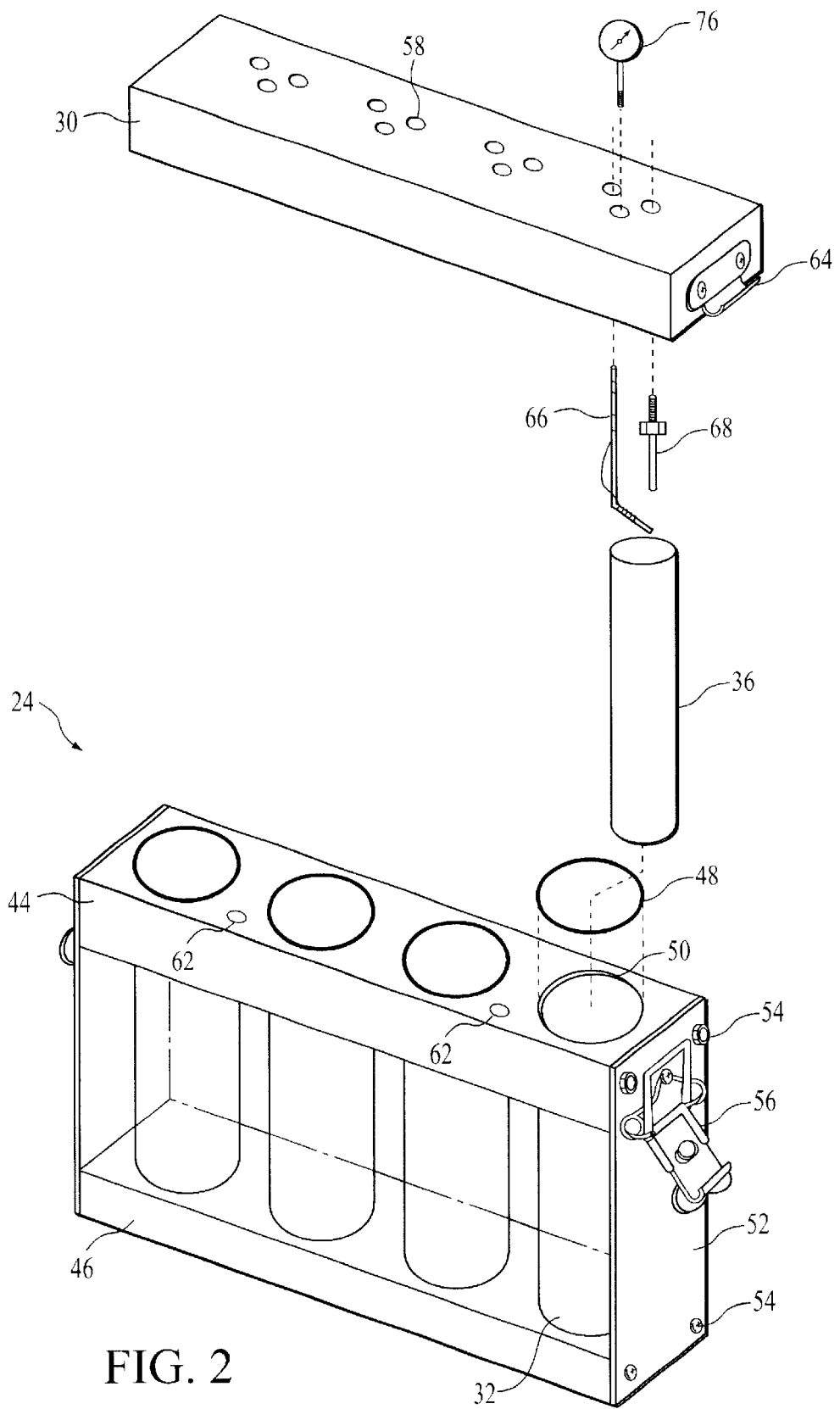
FIG. 2 illustrates an exploded isometric view of a sample collection cassette.

Referring additionally to FIG. 2, a preferred exemplary embodiment of the cassette 24 comprises four discrete collection chambers 32. However, in alternative embodiments, one or more individual chambers 32 are possible in the cassette 24. Each collection chamber 32 in the preferred embodiment is a closed system that is the final separation point of liquid and gaseous phases. Chambers 32 are hollow cylinders constructed of high strength transparent plastic to allow visual monitoring of separation and collection processes. The cassette chambers 32 can be formed of stainless steel or other appropriate laboratory-grade materials. The chambers 32 sit parallel and upright in the cassette 24. Each chamber 32 is constrained at its upper at its upper and lower ends within a molded frame 44, 46. Each chamber 32 is set with the open end surrounded by the upper molded frame 44 and the lower end partially embedded into the lower molded frame 46. Communication of liquid or gaseous phases between chambers 32 is prohibited by seals 48 that are seated in a groove 50 at the top, open end of each chamber 32.

Each collection chamber 32 houses a removable, replaceable liner. A standard glass test tube vial 36 functions as a liner and is seated upright inside each the chamber 32. The closed bottom of a test tube vial 36 rests on the base of the chamber 32 and is easily removable. Once inserted, the top of the test tube vial 36 must be lower than the combined height of a chamber 32 and the internal recessed bore 60 (FIG. 3) of a lid piece 30 when the lid and cassette 24 are engaged. A test tube vial 36 and a chamber 32 are a single pressurized system that communicate through the top of the chamber 32. The test tube vial 36 functions as a disposable liner for the chamber 32 to capture the liquid phase 38 that has separated from the flow stream. The inside of the vial 36 and the annular space of chamber 32 surrounding the vial are equilibrated to the same pressure, which is a range of approximately 20 to 100 psig during separation processes for a flow stream up to 50 ml/min. This arrangement enables sample fraction collection at high pressure using standard laboratory glass test tube vials 36 without a risk of breaking the glass vial inside the chamber 32.

FIG. 2 illustrates the cassette 24, comprising a rectangular frame securing four upright chambers 32. The upper section 44 and lower section 46 of the molded frame hold the chambers 32 in place. The frame is completed by two rigid rectangular end pieces 52 attached to the upper and lower sections. Each end piece 52 is a metal plate fastened to the upper 44 and lower 46 frame sections with machine screws 54. Butterfly latches 56 are installed at te top of both rigid end pieces 52 secure the lid piece 30 to the top of the cassette 26. The lid 30 may be removed manually between sample injections for quick access to, and removal of, chamber liners 36. As illustrated in FIG. 1, the bottom of each chamber 32 has a transfer tube or orifice 33 running completely through the base of a collection chamber and lower frame 46. The orifice 33 through the chamber base 46 can be used to remove liquid phase fluid from a chamber 32 without opening the chamber or depressurizing the chamber 32. The sample discharge port 33 also permits easier drainage and cleaning of the chamber 32 during maintenance of the cassette 24.

Figure 3A:
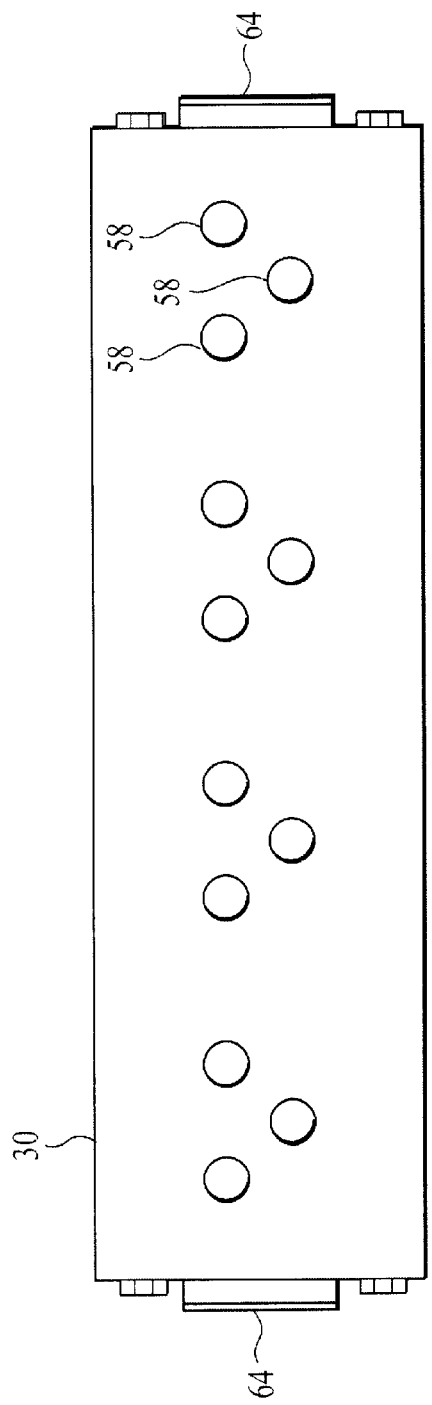
FIGS. 3A and 3B illustrate top and bottom plan views of the cassette lid.
Figure 3B:
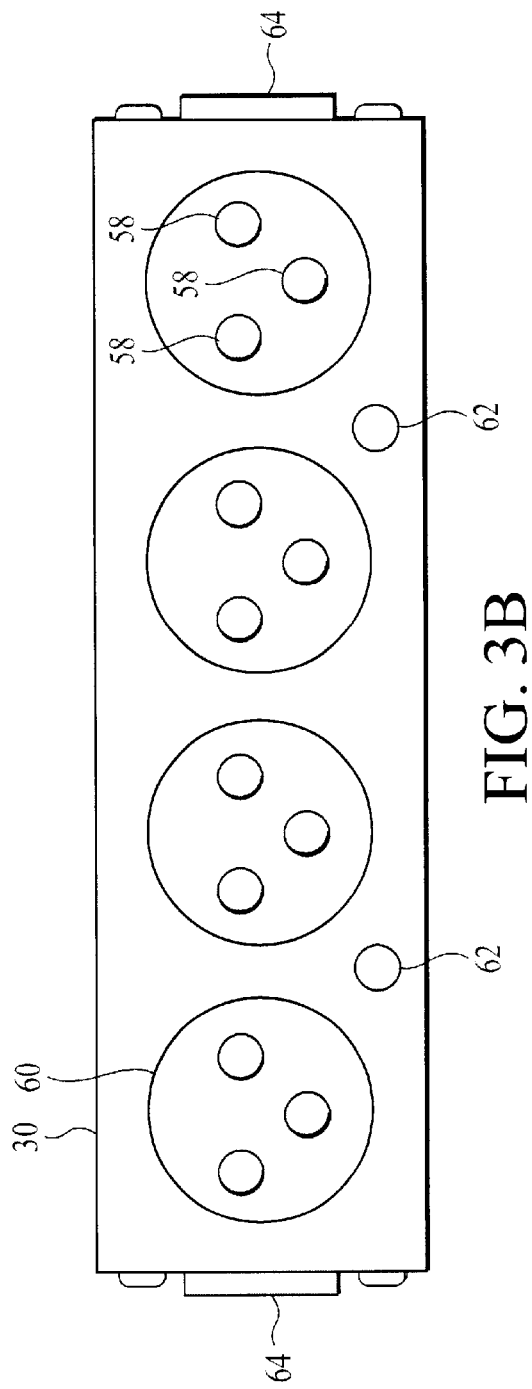

FIGS. 3A and 3B illustrate top and bottom views of the removable cassette lid 30, respectively. The lid 30 has four sets of three boreholes 58 in a triangulated pattern positioned such that each set of boreholes is directly over each of the chambers 32 when the lid 30 is engaged to the cassette 24. The bottom face of the lid 30 has partially recessed bores 60 positioned directly above each chamber 32 when the lid 30 and cassette 24 are engaged. The diameter of a recessed bore 60 is sized slightly smaller than chamber 32 diameters. The recessed bore's 60 perimeter is positioned completely inside of a seal 48 when the lid 30 is fastened to the cassette, as illustrated in FIG. 2. The recessed boreholes 60 allows a test tube 36 to stand taller than the top planar surface of the upper frame section 44 of the cassette 24 so that a test tube 36 may be removed without reaching into a collection chamber 32, thereby possibly cross-contaminating subsequent samples. To guide the lid 30 and cassette base 24 together when engaging, alignment pins 62, illustrated in FIG. 3, are formed on the outer, top surface of the cassette frame 24. Partially recessed bores 63 in the lid 30 receive the alignment pins 62 from the cassette frame 24. Catches 64 for the butterfly latches 56 are attached to each long end of the lid 30.

Inlet transfer tubing 28 carries liquid and gaseous phases into test tube vials 36 housed in each collection chamber 32 of the cassette. Each inlet tube 28 fits through a hole 58 in the lid 30 and inserts into a test tube vial 36. Proper fittings on the tubing 28 provide airtight connections that can also withstand pressure forces in the SFC system. Inlet tubing probes 66 direct elution fluid into a test tube vial 36 and an outlet tube 68 provides an escape route for gas that is under pressure to exit the chamber 32 and discharge to waste collection 26.

In the preferred embodiment, fractions are collected in one chamber 32 of the cassette 24 at a time. During the fractionation process, both the liquid phase and the gas phase discharge into the collection vial 36 where final separation takes place. The pressurization of the collection chamber 32 serves to slow down the velocity the $CO_2$ within the chamber 32. This in turn reduces the magnitude of shear forces occurring between the $CO_2$ gas and the collected liquid at the bottom of the liner 36. With lower shear forces, there is less tendency for the collected liquid to become an aerosol and removed from the collection liner 36 with the existing gas. A similar effect is obtained by the proper angling the inlet transfer line relative tot he collection liner 36 wall. The closer the angle of the tube 66 is to horizontal the lower the observed turbulence at the liquid surface. However, enough angle must be provided to insure the majority of effluent is directed downward rather than upward on the liner 36 wall.

Figure 8A:
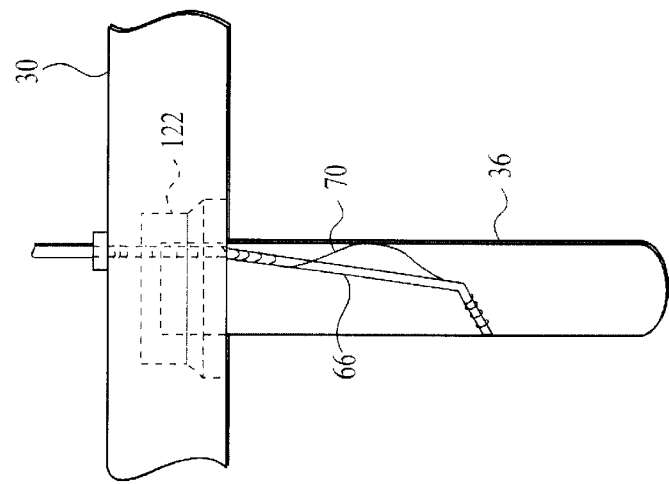
FIGS. 8A and 8B illustrate detailed cross sectional views of transfer tubing before and after insertion into a test tube vial.
Figure 8B:
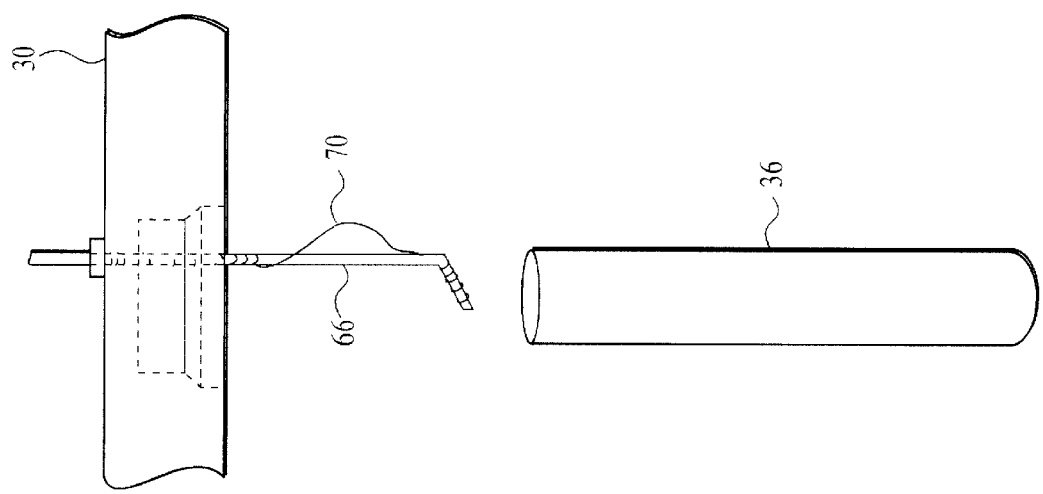

The biphasic elution fluid enters a chamber 32 via a transfer line 28 from the valve system 22. As illustrated in FIGS. 8A and 8B, the tip of the transfer tube 66 is a probe preferentially positioned tangential to the inner wall of the collection vial 36 and with a slight downward angle, usually less than 45 degrees from horizontal. Attached to the probe 66 is a guiding spring wire 70. The spring wire 70 is bowed away from the probe 66. The spring wire 70 acts as a guide for the probe 66 as the probe descends into a test tube vial 36. When the probe 66 is properly inserted into a test tube vial 36, the bowed section of the spring wire 70 contacts the circumferential edge of the open end of a test tube vial 36. As the tubing 66 continues into the test tube vial 36, the spring wire 70 compresses against the inner surface of the vial 36 and pushes the probe 66 towards the opposite side of the vial 36. As a result, the angled tip of the probe 66 is pressed against the inner wall of the test tube vial 36.

The spring wire 70 is extruded from inert materials that will not chemically interfere with collected samples in the test tube vials 36. In an alternative exemplary embodiment, the probe section 66 of the transfer tubing 28 is a rigidly held stainless steel probe attached to the cassette lid 30. Metal versions of probe 66 may be terminated with a larger OD Teflon tube sleeved onto the metal probe to prevent scratching and possible rupture of the inner wall of the collection liner 36.

Both the organic liquid and $CO_2$ gas follows a descending spiral path along the inner wall to the bottom of the collection liner 36. The liquid phase collects at this point and begins to fill the test tube vial 36. The CO2 gas continues in a path up the center of the vial 36 to a vent through the top of the collection chamber 32. A restrictive transfer line attached 72 to the vent causes the CO2 gas to pressurize the collection chamber 32 both inside and surrounding the collection line 36. The degree of back pressurization within the chamber is roughly proportional to the composition of CO2 in the original mobile phase.

The two effects of back pressure and delivery angle combine to reduce aerosol formation in the collected liquid fraction. The success of optimizing these effects determines how close the inlet tube 66 can come to the collection liquid, and thereby determining how high the liners 36 may fill before sample loss becomes a problem. When flow to the chamber 32 is stopped, the chamber depressurizes. Once a chamber is de-pressurized, the test tube vial 36 containing liquid phase may be removed by opening the top lid 30 of the cassette 24.

The outlet line tubing 72 from each chamber 32 is connected to a fixed restrictor 42 to keep pressure inside the chambers 32. The fixed restrictor 42 raises the upstream pressure between approximately 20 and 100 psig depending on CO2 flow rate. Each discharge line 72 passes through a pressure switch 78 to protect against overpressuring and rupturing. Pressure in each chamber is monitored visually with a pressure gauge 76 that is threaded into the lid 58 over each chamber 32. Discharge lines 72 are directed to a waste collection tank 26, from which the CO2 is vented. To increase laboratory safety, the system should not have any exposure of waste effluent, samples, or vented CO2 to ambient laboratory air. The liquids and gasses in the system remain in a contained system that can be directed to a hood or safety exhaust 26 to maximize safety for the technician.

The volume of the captured fractionated liquid phase 38 in the collection vial 36 is controlled manually or automatically. Automatic control in the preferred exemplary embodiment of the valve system 22 and is comprised of one or more valves and an electronic controller. The valve system 22 is designed to offer rapid responses to a manual or automated start/stop signal. A signal can result from detection of a component of interest emerging from the high pressure flow system. A start signal would be generated at the initial detection of the component while a stop signal would be generated at the initial detection of the component while a stop signal would be generated at the loss of detection. The effect of the stop signal is to divert the flow to waste lines 26 or to another chamber 32. An alternative embodiment of a type of start/stop signal may be based on a time-table rather than physical detection of components. The controller may also have features to limit the access time or flow volume allowed to an individual chamber 32. In addition, the controller may allow or prevent the system from cycling back to the original chamber 32 if more fractions are desired than there exist available collection chambers 32.

An alternative exemplary embodiment of the collection cassette and system is illustrated in FIGS. 4 through 7. This embodiment is an automated system that utilizes a robotic arm 80 to replace chamber collection liners 36 after filling with sample fractions. The robotically controlled unit is designed for rapid filling and replacement of chamber liners 36 combined with a long unattended run time. Supply trays 86 of clean test tube vials 36 that function as chamber liners 36 are located within the unit's housing 82. A robotic arm 80 is controlled to replace one or more liners 36 from a row of collection chambers 32 in a collection cassette 84 with liners 36 from a fresh supply rack 86. The robotic arm 80 is mechanized to replace liners 36 on a first row of the cassette 84 while liners 36 on a second row are automatically moved into place. This robotically automated alternative embodiment provides faster sample collection through a minimum of down time to replace liners 36 as well as the ability to collect a greater number of samples during the unattended session.

Figure 4:
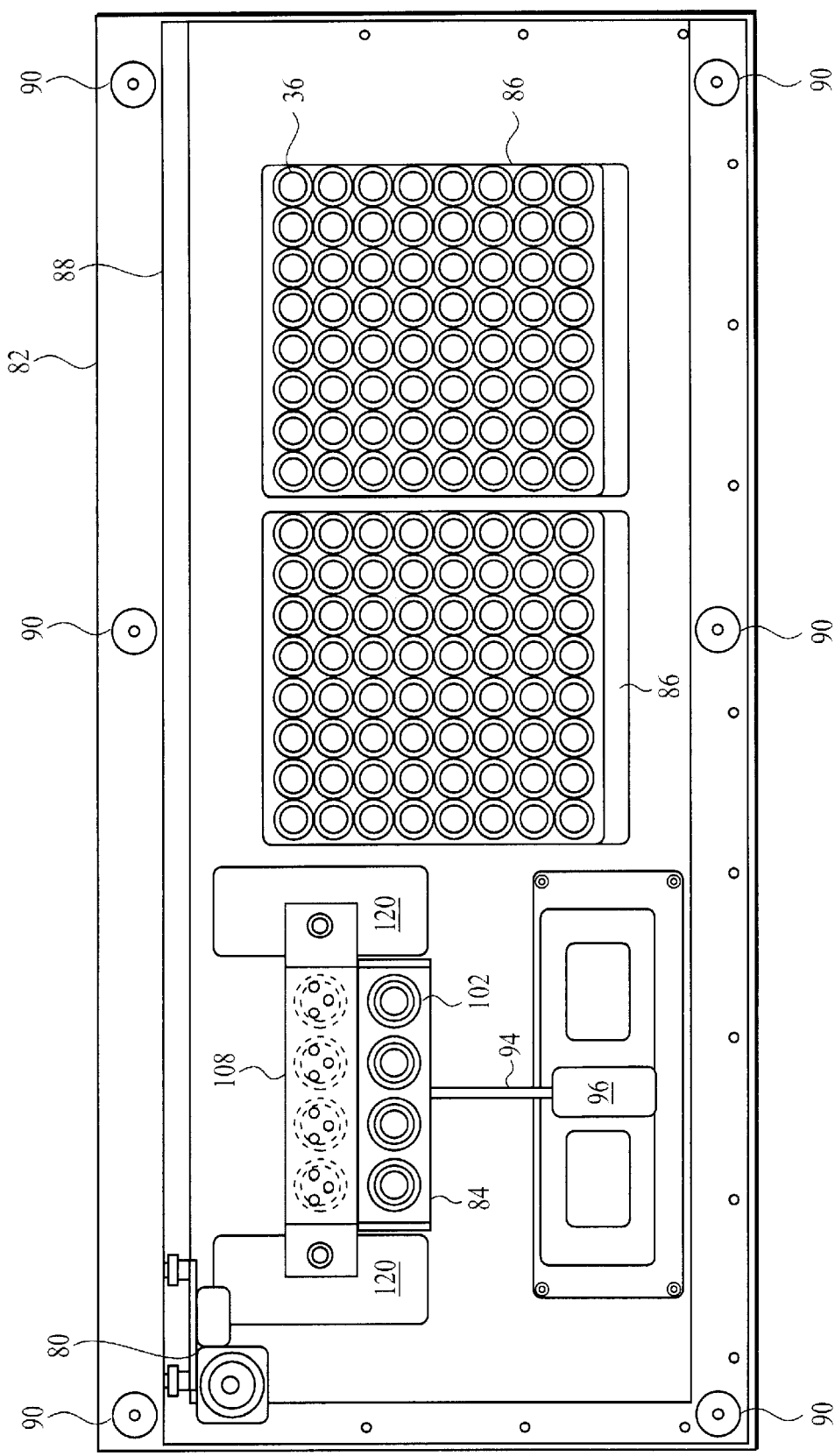
FIG. 4 illustrates a plan view of an alternative exemplary embodiment of an automated fraction collection system.
Figure 5:
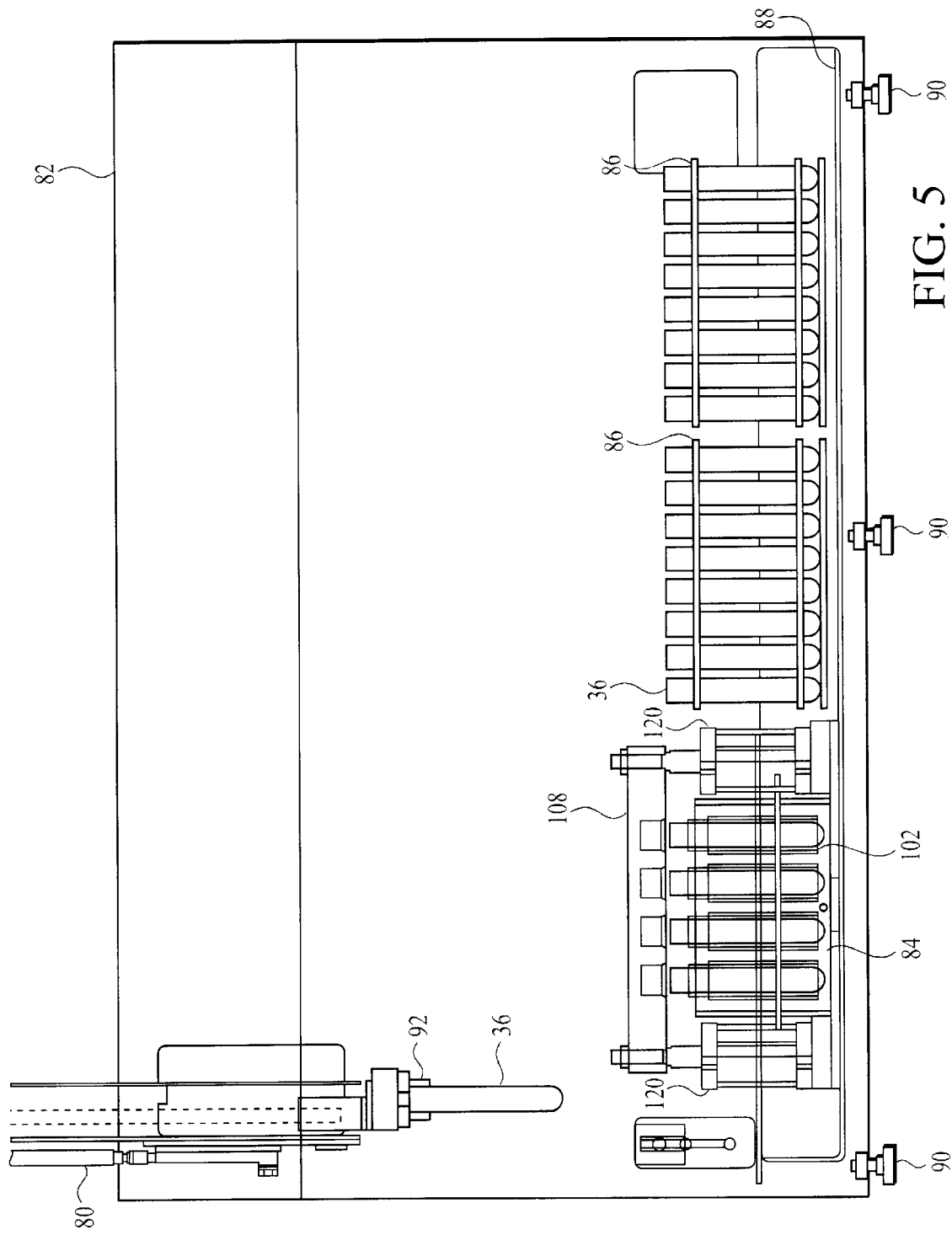
FIG. 5 illustrates a side view of an alternative exemplary embodiment of an automated fraction collection system.

FIGS. 4 and 5 illustrate the plan and side views, respectively, of an automated alternative exemplary embodiment of the SFC sample collection system. The components for the system are partially enclosed with a laboratory-grade housing structure 82 having a raised mounting base 88 within the housing 82. The housing 82 is supported with adjustable feet 90 that are distributed around the base of the housing 82. The feet 90 adjust the level the housing 82 to compensate for uneven or slanted surfaces. Supplies of uncontaminated test tube vials 36 are stored in racks 86 placed on a raised interior base 88 of the housing 82. Each test tube vial 36 is held upright and secure in-place in a rack 86 by molded supports. Each support rack 86 is held upright and secured in-place in a rack 86 by molded supports. Each support rack 86 consists of circular sections attached tangentially to neighboring sections, forming multiple rows and columns. The molded supports loosely secure test tube vials 36 that are held in each circular opening of the racks 86. The vials 36 are maintained equidistant from each neighboring vial to provide adequate spacing for a grabbing jaw 92 on a robotic arm 80 to grasp a vial 36 without interference from a neighboring vial. The spacing also prevents chipping or breakage during movement and replacement of the rack 86. Two racks 86 of test tube vials 36 are illustrated in the Figures, however the system could easily expand to a plurality of racks of the vials 36.

Figure 6:
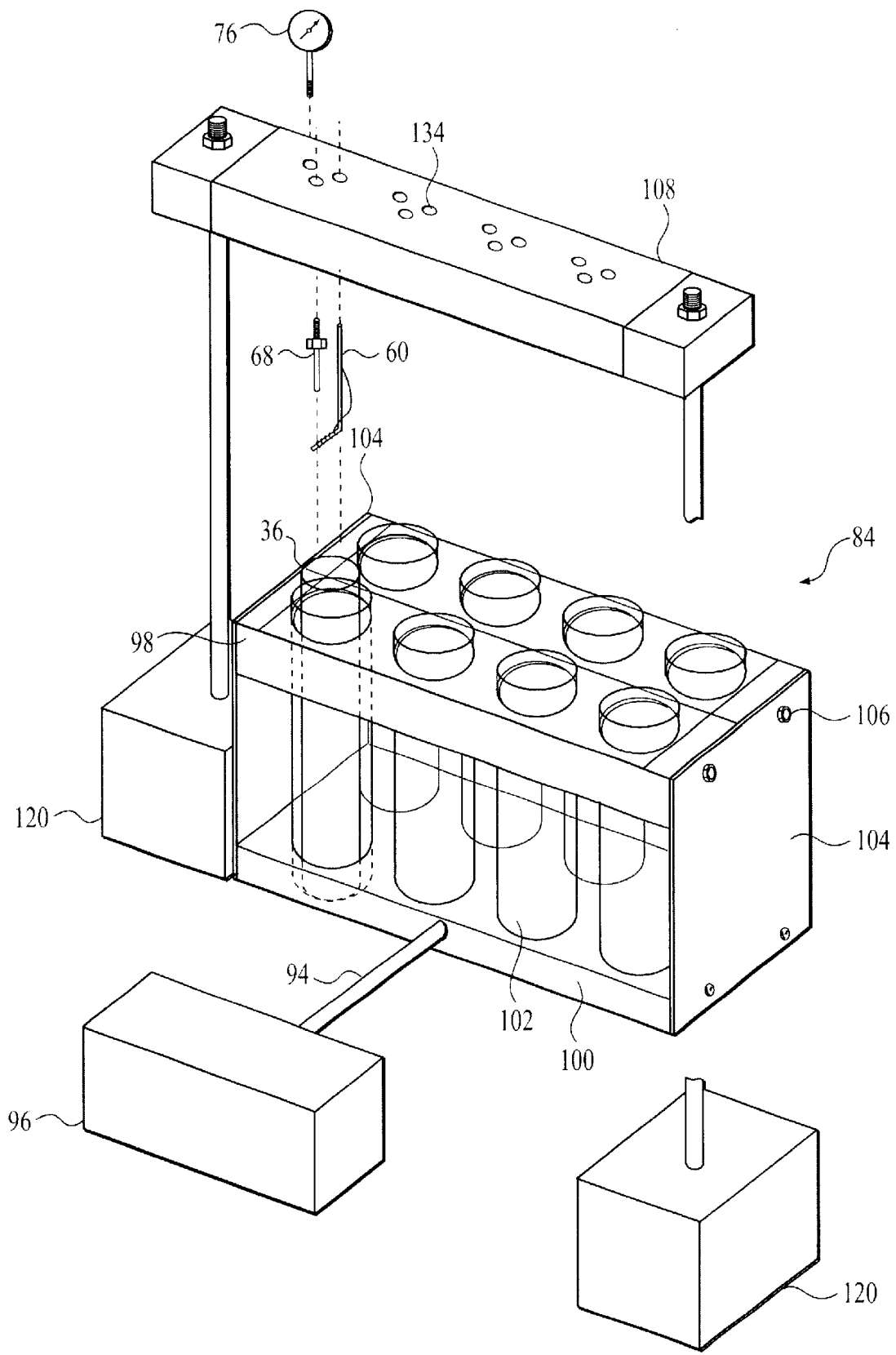
FIG. 6 illustrates an exploded isometric view of a shuttle sample collection cassette, lid, and mechanized controlled movement system.
Figure 7:
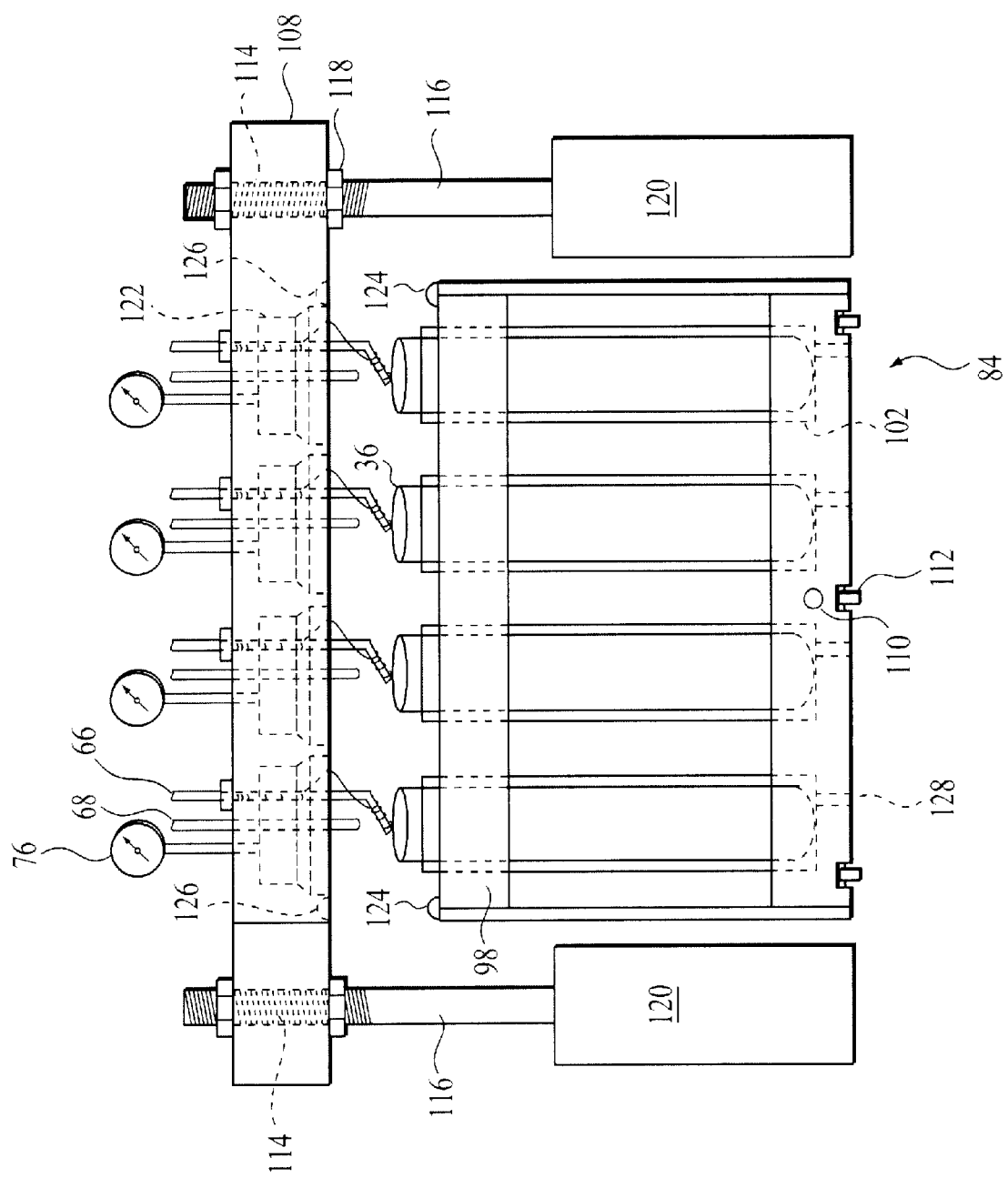
FIG. 7 illustrates a detailed side view of the shuttle cassette and associated mechanical control apparatus.
Figure 10:
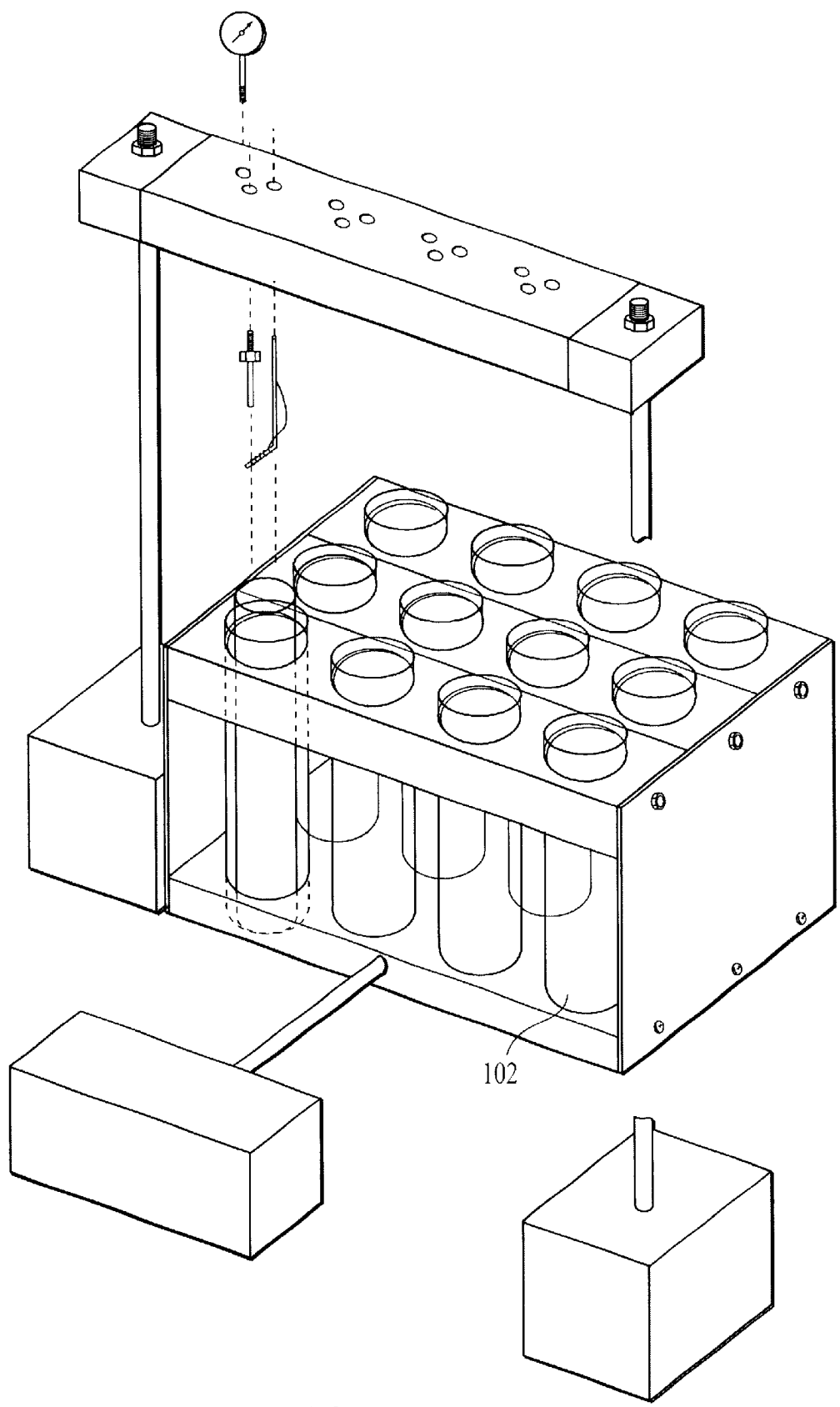
FIG. 10 illustrates an additional alternative embodiment of a shuttle collection cassette for an automated system.

An alternative exemplary embodiment of a cassette 84 and associated system devices is installed on the raised interior base 88. The cassette 84 has a plurality of rows and chambers that are constrained to lateral movements that are automatically controlled with a pneumatic actuator 96. This cassette 84 9s termed the "shuttle cassette," or simply "the shuttle." FIGS. 6 and 7 illustrate the shuttle cassette 84 in isometric and side views, respectively. The shuttle cassette 84 is constructed similar to the exemplary embodiment with an added row of collection chambers 102. The shuttle 84 comprises upper and lower rectangular molded frames 98, 100 supporting a plurality of rows of upright cylindrical collection chambers 102. The shuttle 84 is constructed with two rows of four cylindrical collection chambers 102 in each row. The size of the shuttle 82 can be modified to add additional rows of chambers 102 or additional chambers per row, such as an alternative embodiment featuring three rows of chambers 102 illustrated in FIG. 10. The shuttle cassette 84 is formed on two opposite ends with ridge rectangular plates 104. Each end plate 104 is fastened to the upper 98 and lower 100 molded frame sections with machine screws 106. The shuttle 84 may be constructed with permanent attachments and fittings, however, a shuttle that readily disassembles allows easier and thorough cleaning and replacement of worn or damaged components.

The collection chambers 102 are formed of high-strength transparent plastic, which allows visual monitoring of the collection process inside of each chamber 102. As an alternative, the chambers 102 may be formed of stainless steel or a similar high-strength material compatible with SFC parameters described herein. Each cylindrical chamber 102 is set into the lower molded frame 100 for base support. The upper molded frame section 98 is secured near the open, top end of each chamber 102. Each chamber 102 extends above the top surface of the shuttle 84 at a standardized distance adequate to seal the chambers 102 with an automated lid piece 108. Standard laboratory test tube vials 36 may be inserted into each of the chambers 102 to act as a removable or disposable liner for each chamber.

The automated shuttle cassette 84 is constrained to lateral movements on the inner raised base 88. The lower molded frame section 100, or base, of the shuttle cassette 84 has a horizontally bored hole 110, illustrated in FIG. 7, running perpendicular to the open sides of the shuttle. Offset from the shuttle 84 is an actuator 96 installed on the raised base 88 of the housing unit 82. Attached to the actuator 96 is a rod 94 or controller arm. The rod 94 is constructed of a rigid material, such as stainless steel, and inserts into the bored hole 110 in the base of the shuttle cassette 84, wherein it is firmly attached to the base frame 100. The actuator 96 executes lateral movements of the shuttle 84 according to commands sent from the programmable control system. In an alternative embodiment, the base of the shuttle 100 has small rollers 112 installed around the base, as illustrated on FIG. 7. The rollers 112 are guided laterally by grooved tracks in the base of the housing 88. The tracks not only constrain the movement of the shuttle 84 but also remove tension from the controller arm 94 and actuator 96 gears caused by the shuttle 84 drifting into angled movements caused by uneven friction on the rollers, initial off-center displacement after shuttle 84 installation, or irregularities on the surface of the housing base 88. Other methods of providing constrained lateral movement are possible in alternative embodiments, such as utilizing guide tracks wherein guides on the shuttle 84 are enclosed within tracks riding on ball bearings.

Referring to FIGS. 6 and 7, the lid 108 of the shuttle cassette 84 is automatically controlled to engage a row of collection chambers 102 after the shuttle is moved into place directly below the lid 108 by the lateral actuator 96. In the alternative embodiment, the lid 108 is constructed of stainless steel. However, high-density plastic, or a similar material having equivalent rigidity and composition for use in the collection system, is sufficient. The lid 108 has a hole 114 through each longitudinal end, bored parallel to the vertical axis of the lid. The holes 114 in each end of the lid 108 are sized to fit a threaded rod 116. Two nuts 118 threatened above and below the lid 108 secure the lid to each rod 116. The lid 108 is constrained to move only in the vertical plane. The movements of each rod 116 are controlled by actuators 120 mounted to the raised base of the housing 88. The two pneumatic actuators 120 controlling the lid movements are synchronized to move the rods 116 vertically, thereby raising and lowering the lid 108 onto a row of collection chambers 102 in the shuttle cassette 84.

FIG. 7 illustrates the lid piece 108 raised above the shuttle 84 prior to engagement. The bottom face of the lid 108 has four bores 122 partially recessed into the lid corresponding to four chambers 102 in a row of the shuttle. As the lid 108 is lowered by the pneumatic actuators onto the shuttle 84, each chamber 102 of a row partially inserts into a recessed borehole 122. The lid 108 stops at a programmed point at which the circular edge of each bore 122 engages and seals against the flat upper surface of the shuttle frame 98. Each partially recessed borehole 122 in the lid 108 has a diameter larger than the chambers 102 diameter. As the lid 108 lowers onto the shuttle 84, the recessed boreholes 122 are lined up with the top, open end of each chamber 102. The larger diameter recessed boreholes 123 each totally enclose the open end of each chamber 102. An appropriate sealing O-ring or similar component is placed around the top of each chamber 102, between the top of the shuttle 84 and the lid 108, to provide an airtight and pressure resistant seal when the two components engage. Alignment pins 124 are located on the top surface 98 of a shuttle 84 at both ends of each row of chambers 102. The pins 124 are shaped as half-spheres on the top surface of the shuttle 84 and provide additional protection for shuttle collection chambers 102 from misalignment of the shuttle 84 to the lid 108. As the lid 108 engages onto the shuttle 84, the alignment pins engage corresponding bores 126 in the lid.

A collection chamber 102 is a discrete system that is the final separation point of liquid and gaseous phases. Communication of liquid or gaseous phases between chambers 102 is prohibited through the lid 108 that seals each chamber airtight as it automatically lowers onto a row of chambers in the shuttle cassette 84. Similar to the exemplary embodiment of the cassette, each chamber 102 in the shuttle 84 holds a chamber liner 36 to catch fractional liquid phase. The liner 36 is a standard laboratory test tube vial 36. The closed bottom of the test tube 36 rests at the base of each chamber 102, which rests on the lower molded frame of a shuttle 100. A test tube vial 36 and chamber 102 communicate as a single pressurized system. FIG. 8B illustrates the position of the open end of a vertically disposed test tube vial 36 below the top of a recessed borehole 122 after the lid 108 engages the shuttle 84. The inner pressure of the test tube vial 36 and the chambers 102 annular space surrounding the vial are equilibrated and range from approximately 20 to 100 psig during collection processes. This arrangement enables sample fraction collection at high pressure using standard lower pressure glass or plastic vials by equilibrating the pressure forces inside and outside the vial 36.

As illustrated in FIG. 7, the lower, closed end of each chamber 102 has a sample discharge port 128 running completely through the lower shuttle frame 100. A plug is inserted into each sample discharge port 128 during regular use of the shuttle 84. The sample discharge port 128 permits removal of liquid phase that is collected directly into a chamber 102 without using a liner. By withdrawing liquid phase through the sample discharge port 128, the liquid phase may be collected without disengaging the lid 104 from the shuttle 84. Liquid phase may be evacuated from a chamber 102 under pressure or gravity fed out of a chamber after chamber depressurization.

Inlet 66 and outlet 68 tubing for transferring influent and effluent liquid and gas phases between the shuttle cassette 84 and external transfer lines are illustrated in FIGS. 6 and 7. Inlet 66 and outlet 68 tubing for the shuttle 84 pass through the lid 108. Transfer tubing 66, 68 is constructed from high-pressure stainless steel or equivalent materials. Inlet tubes 66 carry gaseous and liquid phases into a collection chamber 102 under high pressure. Outlet tubes 68 carry separated gaseous phase to a waste tank 26 for venting or disposal. The lid section 108 has four sets of three holes 134 in triangular formations that pass through the lid and are located to correspond with collection chambers 102 when the lid is engaged to the shuttle cassette 84.

In addition to transfer tubing, one of the holes 134 permits measurement of pressure forces inside a chamber with a pressure gauge 76 threaded into the hole 134 from top of the lid 108. The transfer tubing 66, 68 and pressure gauge 136 all have pressure resistant airtight fittings specified to withstand pressure forces created in the SFC system. Transfer tubes 66, 68 installed below the lid 108 insert into a test tube vial 36 when the lid 108 is engaged to the shuttle cassette 84. The tip of each inlet tube 66, or probe, is constrained to an angle less than 45 degrees and wrapped with non-reactive spring wire 70 that is bowed along the vertical section, similar in construction and purpose as described in the preferred embodiment. The spring wire 70 serves to angle the inlet tubing 66 inside a test tube vial 36 by applying pressure forces against the vial's 36 inner wall. As a result, the open tip of the inlet tube 66 is forced tangentially against an opposing inner wall of the vial 36. This configuration of the inlet tube 66 is desirable because it causes the liquid phase that exits the inlet tube 66 to contact a side wall of the vial 36 and swirl down the inner wall of the vial 36 in a spiraling motion. The swirling action provides the final separation process of liquid phase from entrained gaseous phase while preventing re-entrainment and loss of sample fractions from the liquid phases into gaseous phases or aerosol mists that can be carried away with gaseous phases to a waste vent 26.

In an alternative exemplary embodiment, a robotic arm, such as a Cartesian or three-dimensional robotic arm, is programmably controlled to move test tube vials between supply racks and the shuttle cassette collection chambers. FIGS. 4 and 5 illustrate a three-dimensional robotic arm 80 mounted to a wall of the unit housing 82 near the shuttle cassette 84. A host PC or microcontroller issues positioning commands for the arm's movement and controls automated functions. The arm 80 has a jaw 92 to grab and place test tube vials 36 into the shuttle cassette 84 from the test tube supply racks 86. The jaw 92 is controlled to grip test tube vials 36 of specific outer diameter and at specific locations within the unit 82. In the alternative embodiment illustrated in FIG. 5, the robotic arm 80 is gripping one test tube 36 in its jaw 92 to move the test tube between the shuttle 84 and a supply rack 86. To increase the volume of vials 36 exchanged, the gripper jaw 92 could be modified to grip two or more test tube vials, multiple jaws could be placed on a single arm 80, or multiple robotic arms could work on the same embodiment. The arm 80 acts in concert with the automated movements of the shuttle 84. As a row of chambers 102 in the shuttle 84 is engaged to the lid 108, the robotic arm 80 replaces test tube vials 36 in the shuttle that are filled with collected sample fractions with fresh vials 26 from a supply rack 86. When a row of test tubes 36 in the shuttle 84 have been replaced, and the row of vials 36 under the lid 108 have captured liquid phase fractions, a programmable controller signals the pneumatic actuators controlling the lid 120 to disengage and move the lid 108 away from the shuttle 84. The lateral control 96 of the shuttle 84 is then signaled to move the shuttle such that the rows of chambers 102 containing clean, uncontaminated test tube vials 36 correspond to a position underneath the lid 108 prior to engagement. The lid actuators 120 are then signaled to engage the lid 108 again to the shuttle 84, thereby preparing the chambers to receive liquid phase fractions. The robotic arm 80 next grabs vials 36 from the exposed shuttle chambers 102 that contain liquid phase fractions and places them into a supply rack 86. The arm 80 then replaces an uncontaminated vial 36 into each empty chamber 102 until a row of chambers is completely filled with fresh test tubes. This process is repeated for the length of a sample run or until the system is depleted of uncontaminated test tube vials from the supply racks 86.

Figure 9:
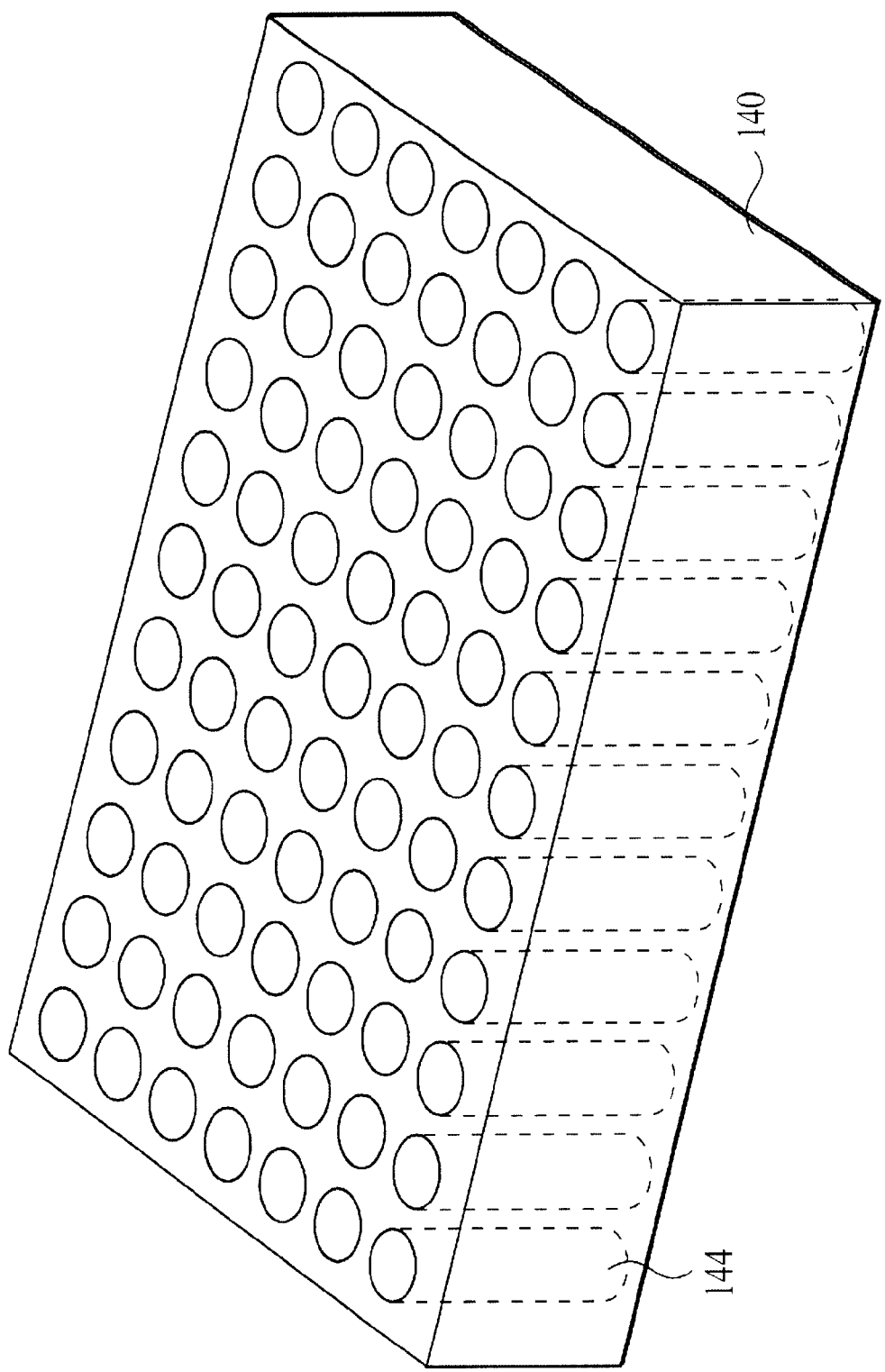
FIG. 9 illustrates an alternative embodiment of an integrated collection cassette having multiple rows of collection chambers.

An alternative embodiment of a collection cassette is illustrated in FIG. 9. An integrated cassette 140 consists of multiple rows of wells 144 in a grid pattern formed similar to a titration tray. The smaller footprint of the integrated cassette 140 can increase the density of collection chambers over the shuttle cassette 84. The integrated cassette 140 also functions as a storage tray for gathered liquid phase fractions. Therefore, time and expense are saved during sampling procedures by removing the steps of the substituting chamber liners 36 and replacing liners from a separate storage area. By modifying the lid 108 and mechanics of the automated collection system, the integrated cassette 140 may serve as its own sample collection cassette and storage tray and can rapidly receive fractions without having to replace liners 36 between each sample injection. The robotic arm 80 in the system may replace integrated cassette 140 units as a whole after a sampling event is completed or chamber wells 144 contain the desired amount of liquid phrase fractions. A plurality of integrated cassettes 140 are stored in the automated collection system providing the means for hundreds of collected fractions during an automated run. A preferred construction of an integrated cassette is a 4×6 chamber array in the deep-well micro titer plate format used commonly in the pharmaceutical industry. Such a format improves automation storage density not only due to more chambers per area, but these chambers are also easily stackable, which gives an added dimension of sample storage capacity. This alternative embodiment is a shuttle cassette tray 140 formed from high-strength materials such as plastic, resin, or stainless steel.

The integrated cassette tray 140 is also advantageous for rapid fraction collection because it can be modified to contain replaceable liners 36 in the wells 144 or use no liners, thereby collecting liquid fractions directly into the wells 144. The integrated cassette 140 can be replaced as a unit after wells 144 are filled with liquid phase fractions.

An alternative embodiment of an automated system using a cassette tray would appear similar to that illustrated in FIG. 4 but with certain modifications. Modifications to the automated system include spacing for a supply of cassette trays 40 instead of test tube racks 86, sizing of the lid piece 108 and associated mechanized controllers 120 and transfer tubing 66, 68, sizing of lateral mechanized controllers 96 for the tray 140 while switching between rows of chambers 144 during fraction collections, and modification of a robotic arm 80 to no substitute filled cassette trays 140 with new trays from a supply area. An alternative to this configuration is having a moveable lid section 108 connected to a robotic arm 80 that engages each flow of chambers in a supply rack of trays 140 without ever moving the trays.

Figure 11:
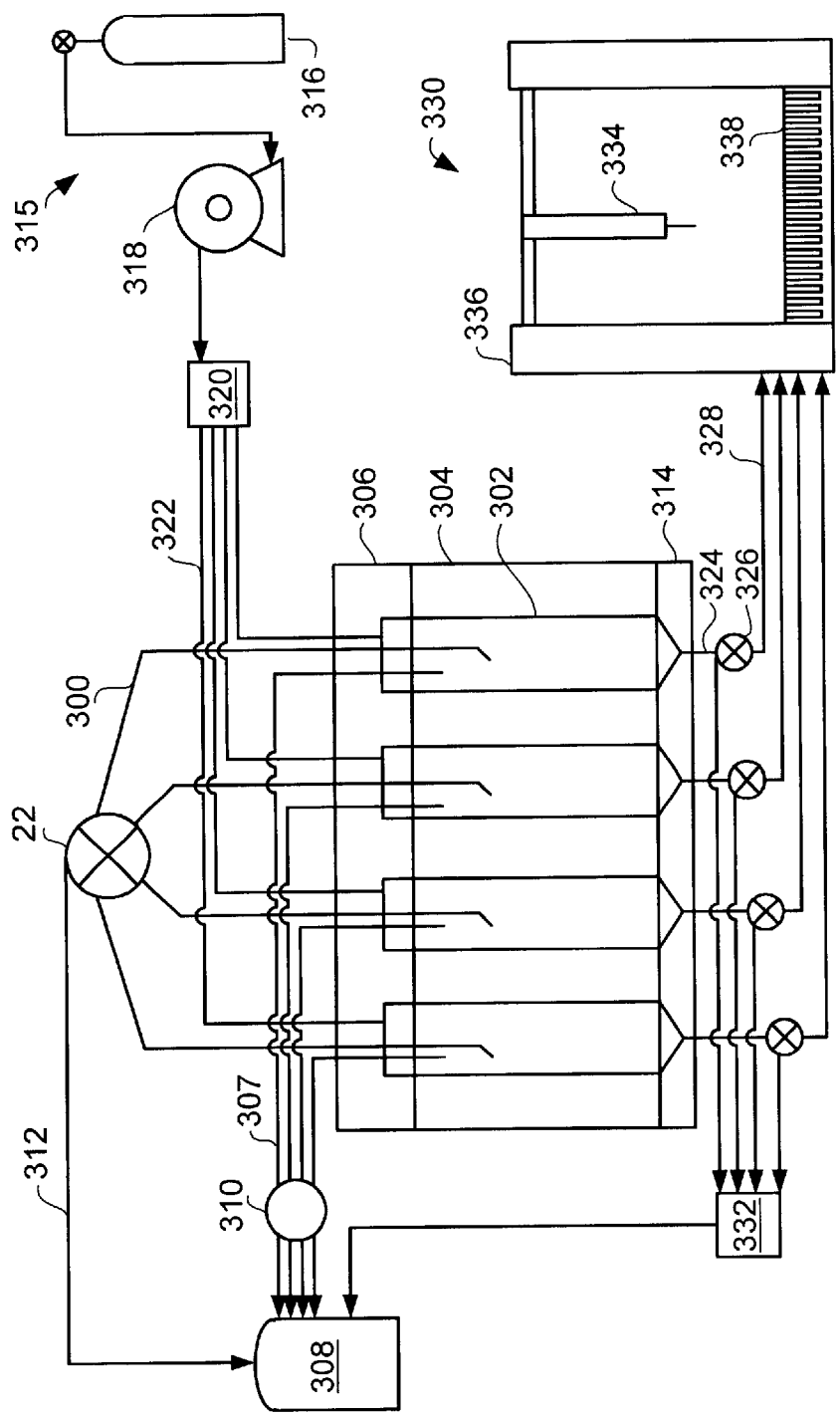
FIG. 11 is a schematic flow diagram of an additional exemplary embodiment having a single cassette bank of collection chambers and a pressure collection system.

An alternative embodiment, illustrated schematically in FIG. 11, receives the mobile phase flow stream through the same valve system 22 of the preferred embodiment. An example of valve 22 is a multi-port selector valve. As mobile phase passes through valve system 22, gas and liquid phases are directed to either a collection chamber 302 or a waste stream container 308. Outlet ports on valve 22 are connected to a plurality of mobile phase flow stream transfer lines 300, and one or more ports on the valve may connect to waste stream line 312.

The alternative embodiment of the cassette 304 is similar in construction and operation to cassette 24 in FIGS. 2 and 6, with the modifications as specified herein. Cassette 304 has one or more individual collection chambers 302 that receive transfer lines 300. Each collection chamber 302 is a closed system that is the final separation point of liquid and gaseous phases from the mobile phase flow stream. Chambers 32 are hollow cylinders constructed of high-strength transparent material to allow visual monitoring of separation and collection processes. As one skilled in the art will recognize, chambers 302 illustrated in FIG. 11 are exemplary embodiments for the present invention. Any type of vessel or container space that is compatible with samples and the SFC system, as described herein, can be used with the present invention to collect liquid phase containing sample fractions. Chambers 302 sit upright and parallel within the cassette 304 frame. Each chamber 302 is constrained at its upper and lower ends. The cassette 304 has a removable lid 306 that is attached to the lower portion of cassette 304.

Mobile phase transfer lines 300 are plastic or stainless steel tubing that carry liquid and gaseous phases into each collection chamber 302 of the cassette 304. Each line 300 passes through lid 306 and is received into each chamber 302. Fittings are used on tubing 300 to provide air- and pressure-tight connections that can withstand pressure forces in the SFC system. Tubing 300 discharges into chambers 302 through a probe on the end of the tube 300 that is preferentially positioned to provide a gentle delivery of liquid phase into a chamber 302 by slowing the velocity of the mobile phase delivery and minimizing turbulence within the chamber. One way to minimize turbulence is to place the flow line tip tangential to the chamber's inner wall at an angle below horizontal. The probe also can be positioned inside of a chamber 302 using a spring mechanism as a guide, similar to the spring wire illustrated in FIG. 5A. The angle and position of the probe directs the liquid phase that is discharging into the chamber 302 into a spiral path that descends along the inner wall to the bottom of the chamber, providing a gentle delivery of the liquid and the opportunity to further separate supercritical gasses from the liquid phase.

Gasses in the collection chamber 302, whether formed by delivery of the mobile phase or separation within the chamber itself, are removed from the chamber through waste discharge line 307. Waste line 307 delivers waste gasses to a waste collection tank 308, where waste products are stored for disposal. Prior to entering waste tank 308, waste discharge lines 307 pass through a back-pressure regulator 310. The regulator 310 maintains pressuring inside chambers 302, which is used for separation and gentle delivery of mobile phase into the chamber. This reduces the magnitude of shear forces occurring between the mobile phase gasses and liquid collected in the chamber 302 that could cause liquid to become carried away into waste line 307. Also, with lower shear forces, there is less tendency for liquid phase in transfer line 300 to aerosolize and become trapped with gasses exiting the chamber 302 to waste tank 308. To increase laboratory safety, the system should not have any exposure of waste products to ambient air and laboratory personnel. In the present invention, gasses in the system should remain in a contained system.

The volume of collected liquid phase in a chamber 302 is controlled manually or automatically. A controller can direct mobile phase flow through valve 22 between chambers 302 or to waste tank 308. The valve system 22 is designed to offer rapid response to a manual or automated start/stop signal. A signal can result from detection of a component of interest from an injected sample eluted through column 214. A start signal could be generated at the initial detection of the component to direct mobile phase flow to a chamber, while a stop signal could be generated at the loss of component detection. The effect of the stop signal is to divert the flow to waste line 312 or, if further collection of mobile phase is desired, to a different chamber 302.

An alternative method to issuing a start/stop signal is based on a time table of injection to elution times rather than detection of the eluted components. A system controller saves elution periods of sample solutes through column 214 that are targets of collection processes. The time period between injection of a discrete sample volume through the injection valve 212 and the appearance of the leading edge of the targeted solute's peak concentrations through column 214 and detector 216 is measured and recorded. For example, a sample injection may produce peaks at five minute intervals after injection. If a first peak appears at a five minute time period from injection and the elution lasts for a two minute time period, the separation times would normally allow one sample injection approximately every eight minutes. However, injections are optimized for rapid collection of eluted solutes. In the example, the controller automatically injects samples every two minutes for elutions of specific solutes, regardless of whether the entire chromatographic results of the previous injections have completed their runs. This process results in an improvement of three to ten times over the rate at which samples may be separated and retained by the collection system over prior methods.

To remove liquid phase elutions from a chamber 302, liquids are displaced from each chamber to a separate collection system 330. To remove liquids from a chamber, a separate displacement force is applied to a chamber. The bottom ends of each chamber 302 are angled or funneled such that liquid phase could drain into a sample collection line 324 attached to the bottom end of a chamber. A multi-valve 326, such as a three-way valve, keeps flow line 324 normally closed. After liquid phase has filled chamber 302 to a pre-determined level, valve 326 is opened to line 328 and a pressure force is applied to the chamber. Pressure in a chamber is delivered from system pump 315 supplying pressurized flow using supply gas from tank 316, or alternatively uses ambient air preferably passed through a filter. Distributor 320 containing valves, or switches, to direct pressure flow to a specific chamber 302 through a displacement force flow line 322. Pressurized gas enters a chamber 302 near the top end to push liquid phase out the bottom end and into sample collection line 324. Valve 326 then directs liquid phase to flow line 328 which is received by automated sample collection system 330. When liquid in a chamber 302 must be purged, and delivery to the automated collection system 330 is unavailable, or unwarranted, valve 326 directs liquid phase flow to waste collection tank 308. Flow lines to waste tank 308 could be separated up to the tank 308, however a manifold 332 combining flow lines from valve 326 into one line can increase efficiency.

Alternative systems for removing liquid phase from a chamber 302 include displacement by vacuum forces or draining by gravity. Vacuum forces may be applied by pulling a vacuum on a chamber containing liquid phase, thereby drawing liquid into sample collection lines 324 and 328. Vacuum is applied until the mechanism associated with robotic arm 334 controls the movement of the fluid. An additional system for removing liquid phase by a vacuum force is using a dip tube placed into a chamber from the top. The dip tube is inserted to the bottom of a chamber and removes liquid phase to the sample collection system 330. Gravity may be used to drain liquid phase from the bottom of a chamber 302. After opening valve 326, liquid phase is drained into the collection system 330. If the head level in robotic arm 334 is below the head level in flow line 328, then the liquid phase could be placed into collections containers 338 by gravity as well.

The automated sample collection system 330 is a separate system from cassette 304. Collection system 330 distributes liquid phase using a robotic arm 334. Examples of a robotic arm 334 include a Cartesian or three-dimensional robot that is connected to supports 336 and is programmably controlled to dispense liquid phase into collection containers 338. Robotic arm 338 is automatically moved by a controller that issues positioning commands for the arm's movement and dispensing functions. Sample collection containers 338 are any type of container desired for storage and transportation of discrete volumes of sample fractions. Examples of containers 338 include test tube vials, sample vials, and microtitration trays. A microtitration tray has the advantage of a smaller footprint that contains hundreds of wells, which increases the density of collection containers over a limited area. A plurality of microtitration trays can be held in the automated collection system, thereby providing the means for hundreds of collected sample fractions during an automated run.

Figure 12:
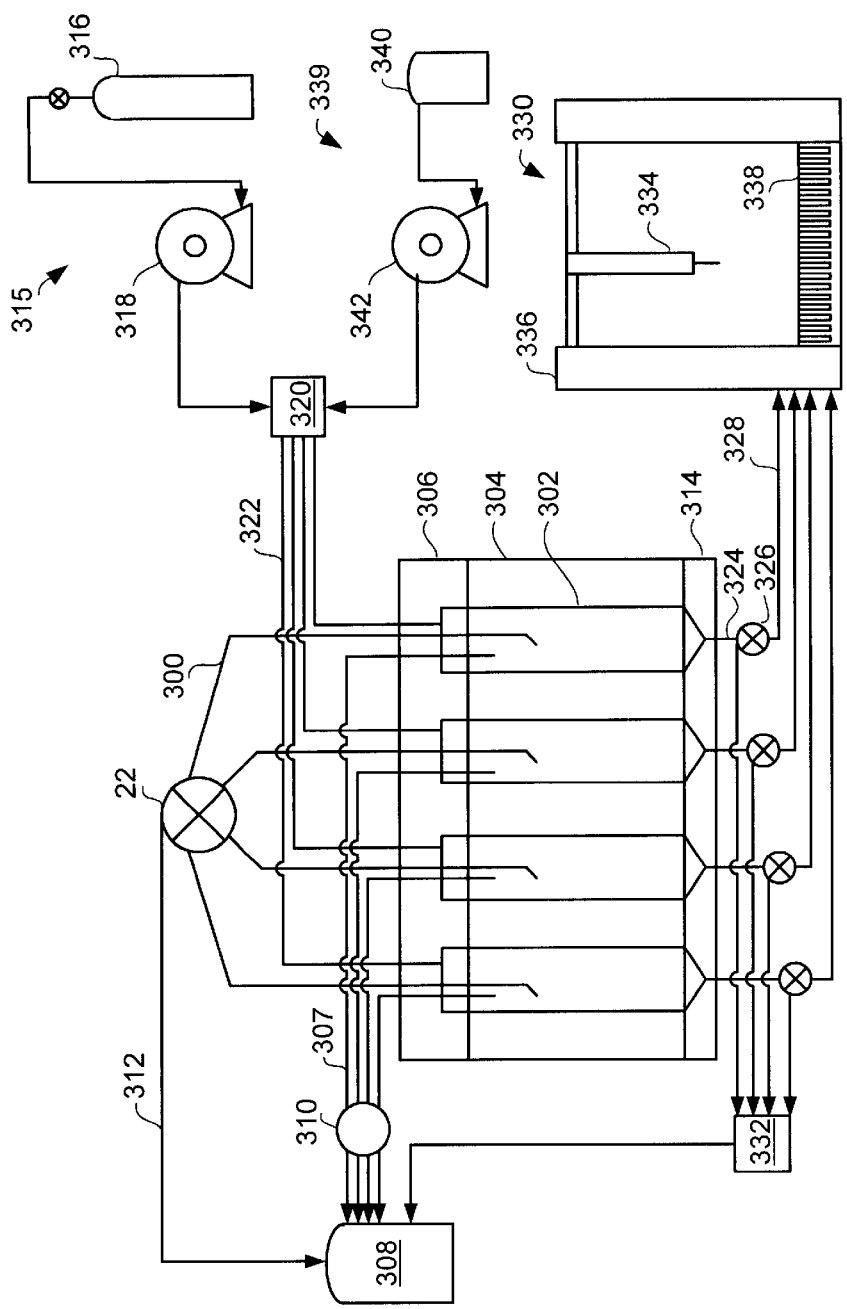
FIG. 12 is a schematic flow diagram of an additional exemplary embodiment having a single cassette bank of collection chambers and a pressure collection system and cleaning system.

Referring to FIG. 12, a renewal system 339 of the alternative embodiment is illustrated in the schematic diagram. The renewal system 339 processes cassette chambers 302 back to uncontaminated states after removal of liquid phase sample fractions. The renewal system may be automated to wash a chamber 302 after removal of liquid phase, or at any time between sample collection into a chamber 302. The system 339 has a supply tank 340, that stores cleaning solutions. Solutions in tank 34 may include gasses as well as liquids. Tank 340 feeds pump 342 which pumps cleaning solution into cassette chambers 302. Cleaning system 339 pumps solution through the same distributor 320 and flow lines 322 used by pressure pump 318. This permits addition of cleaners to chambers 302 without adding additional lines. An alternative embodiment, that is not illustrated, uses flow lines separate from lines 322 to deliver solution from pump 342 to each chamber.

Solutions from the cleaning system pump 342 enter into a chamber 302 and are distributed to wash the walls of a chamber by any means known in the art. Spent cleaning solution is removed from each chamber similar to the liquid phase sample fractions. Solutions are directed into sample collection flow line 324 through the bottom end of a chamber 302 by the angled or funneled bottom of the chamber. Valve 326 is normally closed during washing procedures and then opened to direct solutions to waste discharge manifold 332 while blocking flow to sample collection system 330. Spent solutions are then directed to waste collection tank 308, or a similar waste product disposal. All flow lines 322, 324 and chamber 302 are purged of spent cleaners by engaging the pressure flow system from pump 318, thereby flushing liquids out of chambers or drying residual elements. To further flush the chambers, filtered water could be pumped through the cleaning system 339 and disposed of into waste tank 308.

Figure 13:
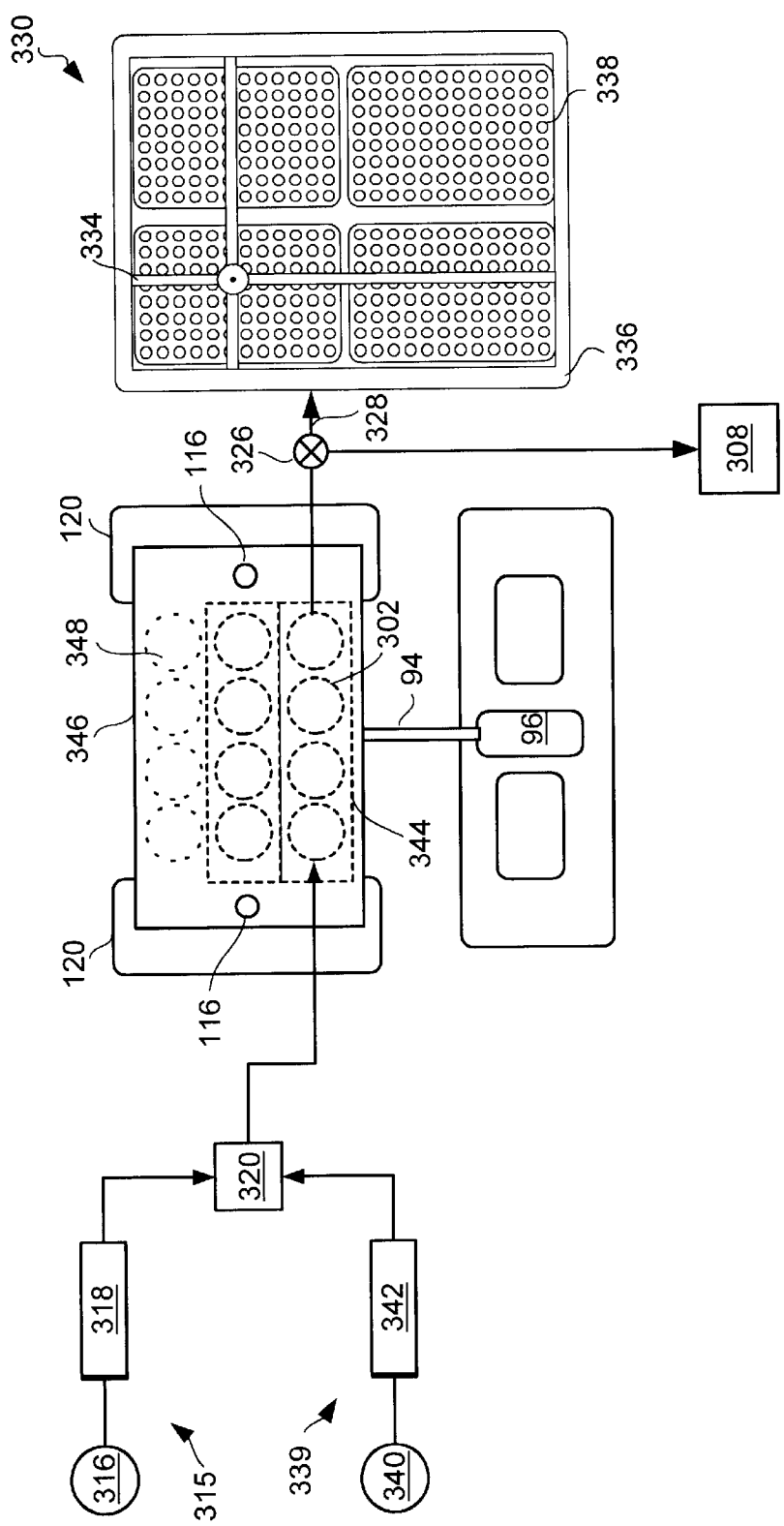
FIG. 13 is a schematic flow diagram of an additional exemplary embodiment having multiple banks of collection chambers in a shuttle cassette with and a pressure collection system and cleaning system.

FIG. 13 is a schematic diagram illustrating a plan view of an alternative embodiment of a shuttle cassette 344 having modifications from the shuttle cassette 84 in FIGS. 4 and 6 as described herein. Shuttle cassette 344 combines two cassettes, having a bank of four chambers each, set in parallel. Similar to shuttle cassette 84, the alternative embodiment 344 is connected to a rod, or controller arm 94, that is controlled by an actuator 96. Actuator 96 executes lateral movements of the shuttle 344 according to commands sent from a programmable control system. The lid 346 of the alternative embodiment is sized to allow engagement of up to three banks of chambers 302 simultaneously, however only two banks of chambers are engaged at any one time. Lid 346 is constrained to move in the vertical plane. The movement of each rod 116 is controlled by actuators 120. For example, pneumatic actuators 120 at each short end of the lid 346 are synchronized to move rods 116 vertically, thereby raising and lowering the lid 346 onto the chambers 302 of the shuttle cassette 344.

Figure 14:
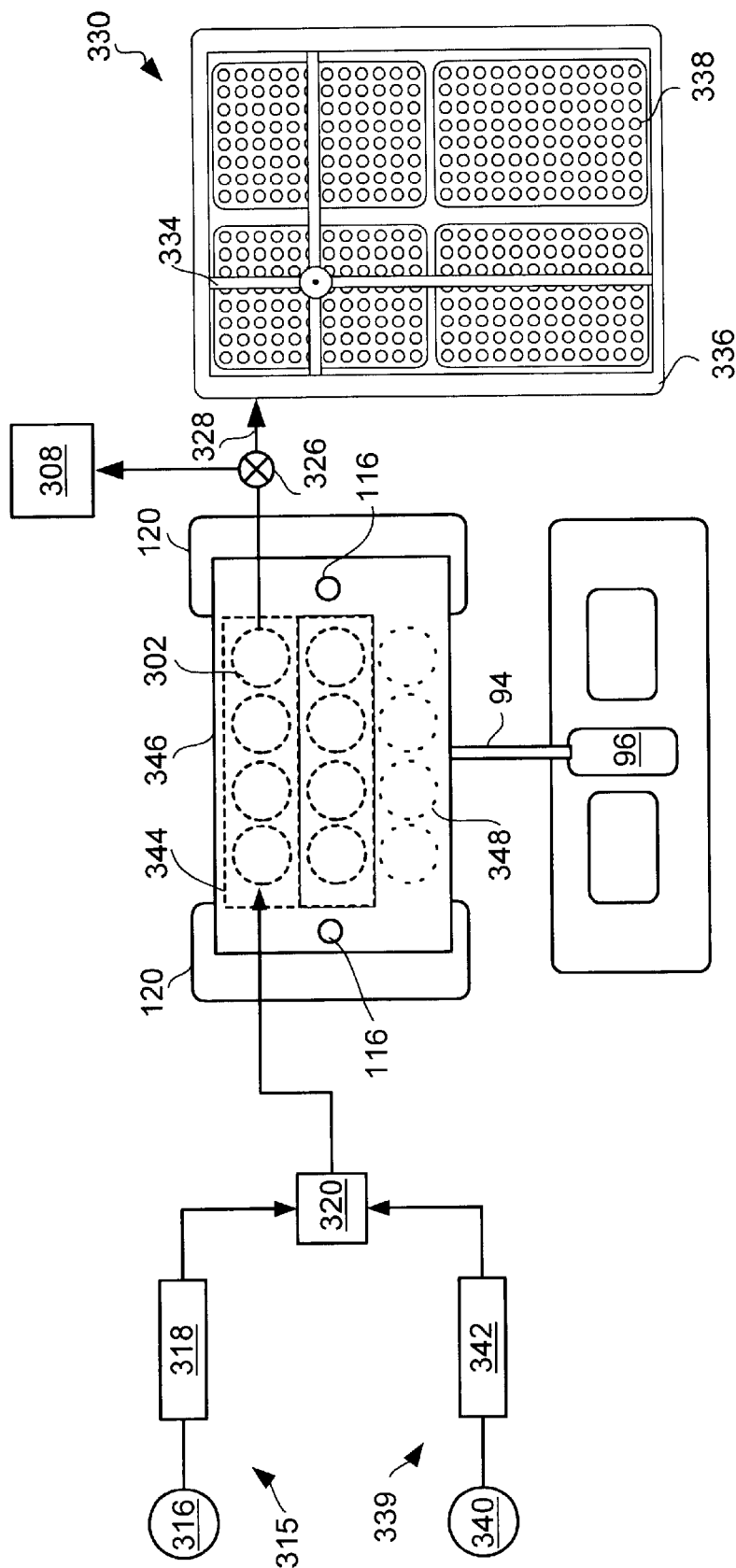
FIG. 14 the diagram of FIG. 13 with the shuttle cassette moved laterally.

Shuttle cassette 344 uses the separate sample collection system 330, pressure system 315, and cleaning system 339 in a more efficient manner than a single cassette 304 through automation by alternating the collection of liquid phase into one bank of chambers while moving liquid phase to the sample collection system 330 from the second bank. Using the actuators 96, 120 the shuttle moves chambers laterally underneath lid 346. The shuttle has two positions under lid 334. A first position is illustrated in FIG. 13, where chamber-receiving bores 348 under the lid are empty. A second position is illustrated in FIG. 14, where the shuttle has moved laterally such that the unengaged row of chamber-receiving bores are on the opposite side of lid 346. As can be seen in the schematics, a bank of chambers is always engaged in the center position of the lid 346, between actuator rods 116, whether in the first position of FIG. 13 or the second position of FIG. 14. The center position is the row of chambers that receives mobile phase flow stream 300, containing liquid phase, from distribution valve 22. The outer bank of chambers in each position is the bank from which the collected liquid phase is removed under pressure to collection containers 338 and which are washed with cleaning solutions from the cleaning system 339. Optimally, the two rows of chambers are executing their functions simultaneously: the center positioned bank fills with liquid phase while the liquid phase in the outer row is removed and the chamber is washed and renewed for the repositioning into the center position.

After liquid phase is collected in a bank of chambers 302, the shuttle moves the bank into positioning for application of the pressure system 315 and wash system 339. Pressure is applied from pump 318 through distributor 320 to each chamber 302. Valve 326 is opened, directing liquid phase to separate sample collection system 330. The robot arm 334 automatically fills sample collection containers 338 with liquid phase from each chamber. After removal of liquid phase to sample containers, the chamber is washed pump 342 pumps solution into each chamber, thereby washing the chamber walls. Cleaning solution is purged from the chamber by invoking the pressure system 315 on each chamber turning valve 326 and flushing spent solution to the 308. To create a faster, more efficient collection system, liquid phase collection into center position chambers and the liquid phase removal and chamber renewal steps on the outer chamber rows are performed as simultaneous as is practicable.

As can be understood from the above description, the sample collection system has several advantages, for example: it provides simplified prep-SFC sample collection; it collects only fractions of interest from the injected sample; it collects purified samples into removable, inexpensive, and disposable collection containers; it provides extremely efficient and controllable gas and liquid phase separation, thereby providing up to 98% consistent sample recovery; it is environmentally friendly and economical because it eliminates additional use of solvents to collect, trap, or recover samples, and clean unnecessary associated mechanical separation equipment; it allows high speed, high volume, and high purity SFC sample collection.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed:

1. A system for collecting samples from a flow stream containing a mixture of highly compressed gas, compressible liquid or supercritical fluid and a relatively incompressible liquid comprising:

means for controlling the pressure, temperature and velocity of the flow stream to enhance separation processes of a monophasic fluid mixture into separate gaseous and liquid phases:
  a collection chamber that collects liquid phase from the flow stream;
  a displacement force line connected to the chamber that applies a displacement force to the liquid phase, where the displacement force removes the liquid phase from the chamber; and
  a sample collection container that receives liquid phase removed from the chamber.

2. The system of claim 1, further comprising:
a robotic arm that receives liquid phase that is removed from the chamber and automatically dispenses the liquid phase into the collection container.

3. The system of claim 1, wherein:
a plurality of the collection chambers that are secured in a support frame having a removable lid, thereby forming a cassette bank of chambers.

4. The system of claim 1, further comprising:
the displacement force is one of the following: a pressure force, a vacuum force, or gravity.

5. The system of claim 1, further comprising:
the collection container is one of the following: a test tube, a microtitration tray, or a sample vial.

6. The system of claim 1, further comprising:
a cleaning system for resetting the collection chamber to an uncontaminated state by automatically cleaning the chamber and thereafter purging cleaner contents to a waste stream.

7. The system of claim 1, further comprising:
a probe that delivers liquid phase into the chamber at an angle below horizontal and an angle tangential to the inner wall of the chamber to promote gentle delivery of liquid phase into the chamber.

8. A system for collecting samples from a flow stream containing a mixture of highly compressed gas, compressible liquid or supercritical fluid and a relatively incompressible liquid comprising:
  means for controlling the pressure, temperature and velocity of the flow stream to enhance separation processes of a monophasic fluid mixture into separate gaseous and liquid phases:
    a collection chamber that collects liquid phase from the flow stream;
    a displacement force line connected to the chamber that applies a displacement force to the liquid phase, where the displacement force moves the liquid phase from the chamber to a
    a sample collection container; and
    a pump that injects cleaning solution into a collection chamber for resetting the collection chamber to an uncontaminated state.

9. The system of claim 8, further comprising:
a robotic arm that receives liquid phase that is removed from the chamber and automatically dispenses the liquid phase into the collection container.

10. The system of claim 8, wherein:
a plurality of the collection chambers that are secured in a support frame having a removable lid, thereby forming a cassette bank of chambers.

11. The system of claim 8, further comprising:
the displacement force is one of the following: a pressure force, a vacuum force, or gravity.

12. The system of claim 8, further comprising:
the collection container is one of the following: a test tube, a microtitration tray, or a sample vial.

13. The system of claim 8, further comprising:
a probe that delivers liquid phase into the chamber at an angle below horizontal and an angle tangential to the inner wall of the chamber to promote gentle delivery of liquid phase into the chamber.

14. A system for collecting samples from a flow stream containing a mixture of highly compressed gas, compressible liquid or supercritical fluid and a relatively incompressible liquid comprising:
  means for controlling the pressure, temperature and velocity of the flow stream to enhance separation processes of a monophasic fluid mixture into separate gaseous and liquid phases;
  a valve for redirecting the flow stream into a collection chamber;
  a pressure supply system for applying a displacement force onto liquid phase collected in a chamber, thereby removing the liquid phase from the chamber;
  a sample collection container separate from the chamber for receiving displaced liquid phase; and
  a pump that injects cleaning solution into a collection chamber for resetting the collection chamber to an uncontaminated state by introducing a cleaning solution into the chamber, cleaning the chamber, and discharging the cleaning solution to a waste flow stream.

* * * * *